US010849885B2

(12) United States Patent
Hirawat et al.

(10) Patent No.: US 10,849,885 B2
(45) Date of Patent: *Dec. 1, 2020

(54) METHODS FOR DOSING AN ORALLY ACTIVE 1,2,4-OXADIAZOLE FOR NONSENSE MUTATION SUPPRESSION THERAPY

(71) Applicant: PTC THERAPEUTICS, INC., South Plainfield, NJ (US)

(72) Inventors: Samit Hirawat, Chatham, NJ (US); Langdon Miller, Seattle, WA (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 222 days.

This patent is subject to a terminal disclaimer.

(21) Appl. No.: 16/208,663

(22) Filed: Dec. 4, 2018

(65) Prior Publication Data

US 2019/0099405 A1   Apr. 4, 2019

Related U.S. Application Data

(63) Continuation of application No. 15/875,296, filed on Jan. 19, 2018, now Pat. No. 10,172,836, which is a continuation of application No. 15/643,724, filed on Jul. 7, 2017, now Pat. No. 9,877,952, which is a continuation of application No. 15/345,748, filed on Nov. 8, 2016, now Pat. No. 9,737,513, which is a continuation of application No. 14/972,269, filed on Dec. 17, 2015, now Pat. No. 9,522,137, which is a continuation of application No. 11/974,068, filed on Oct. 11, 2007, now Pat. No. 9,226,919.

(60) Provisional application No. 60/851,450, filed on Oct. 12, 2006.

(51) Int. Cl.
| | | |
|---|---|---|
| *A61K 31/4245* | (2006.01) | |
| *A61K 9/00* | (2006.01) | |
| *A61K 47/02* | (2006.01) | |
| *A61K 47/10* | (2017.01) | |
| *A61K 47/12* | (2006.01) | |
| *A61K 47/26* | (2006.01) | |
| *A61K 47/32* | (2006.01) | |
| *A61K 47/34* | (2017.01) | |
| *A61K 47/36* | (2006.01) | |
| *A61K 47/38* | (2006.01) | |

(52) U.S. Cl.
CPC ........ *A61K 31/4245* (2013.01); *A61K 9/0095* (2013.01); *A61K 47/02* (2013.01); *A61K 47/10* (2013.01); *A61K 47/12* (2013.01); *A61K 47/26* (2013.01); *A61K 47/32* (2013.01); *A61K 47/34* (2013.01); *A61K 47/36* (2013.01); *A61K 47/38* (2013.01)

(58) Field of Classification Search
CPC .......................... A61K 31/4245; A61P 35/00
See application file for complete search history.

(56) References Cited

U.S. PATENT DOCUMENTS

| | | |
|---|---|---|
| 6,660,753 B2 | 12/2003 | Van Wagenen et al. |
| 6,759,538 B2 | 7/2004 | Singh et al. |
| 6,992,096 B2 | 1/2006 | Karp et al. |
| 7,112,595 B2 | 9/2006 | Wagenen et al. |
| 7,153,880 B2 | 12/2006 | Singh et al. |
| 7,202,262 B2 | 4/2007 | Karp et al. |
| 7,304,080 B2 | 12/2007 | Karp et al. |
| 7,419,991 B2 | 9/2008 | Karp et al. |
| 7,678,922 B2 | 3/2010 | Almstead et al. |
| 7,683,082 B2 | 3/2010 | Karp et al. |
| 7,772,259 B2 | 8/2010 | Karp et al. |
| 7,863,456 B2 | 1/2011 | Almstead et al. |
| 8,716,321 B2 | 5/2014 | Hirawat et al. |
| 9,226,919 B2 | 1/2016 | Hirawat et al. |
| 9,522,137 B2 | 12/2016 | Hirawat et al. |
| 9,737,513 B2 | 8/2017 | Hirawat et al. |
| 9,877,952 B2 | 1/2018 | Hirawat et al. |
| 2005/0169992 A1 | 8/2005 | Jao et al. |
| 2007/0010553 A1 | 1/2007 | Lehmann |

FOREIGN PATENT DOCUMENTS

WO   WO 2006/110483   10/2006

OTHER PUBLICATIONS

U.S. Appl. No. 60/149,464, filed Aug. 19, 1999, Van Wagenen et al.
U.S. Appl. No. 60/269,847, filed Feb. 21, 2001, Van Wagenen et al.
U.S. Appl. No. 60/350,107, filed Nov. 2, 2001, Singh et al.
U.S. Appl. No. 60/405,472, filed Aug. 23, 2002, Singh et al.
"A Phase 2 Study of PTC124 as an Oral Treatment for Nonsense-Mutation-Mediated Cystic Fibrosis," ClinicalTrials.gov; Aug. 3, 2006.
"A Phase 2 Study of PTC124 as an Oral Treatment for Nonsense-Mutation-Mediated Duchenne Muscular Dystrophy," ClinicalTrials.gov; Oct. 5, 2006.
"PTC Therapeutics Presents Data from Phase 1 Multiple-Dose Study of PTC124 at the 2005 American Academy of Neurology Meeting," PTCT News; Apr. 11, 2005.
Announcement by PTC Therapeutics, Inc. and Genzyme Corporation dated Mar. 3, 2010.
Auld et al., 2009, "Mechanism of PTC124 activity in cell based luciferase assays of nonsense codon suppression," *PNAS Early Edition*:1-6 (document sent via fax Jan. 28, 2009).
Auld et al., 2010, "Molecular basis for the high-affinity binding and stabilization of firefly luciferase by PTC124," *PNAS Early Edition*:1-6.

(Continued)

*Primary Examiner* — Barbara P Badio
(74) *Attorney, Agent, or Firm* — Jones Day

(57) ABSTRACT

The present invention relates to specific doses of and dosing regimens for using a 1,2,4-oxadiazole benzoic acid compound in treating or preventing diseases associated with nonsense mutations. In particular, the invention relates to specific doses and dosing regimens for the use of 3-[5-(2-fluoro-phenyl)-[1,2,4]oxadiazol-3-yl]-benzoic acid in mammals having diseases associated with nonsense mutations.

10 Claims, 2 Drawing Sheets

(56) References Cited

OTHER PUBLICATIONS

Figure 1:
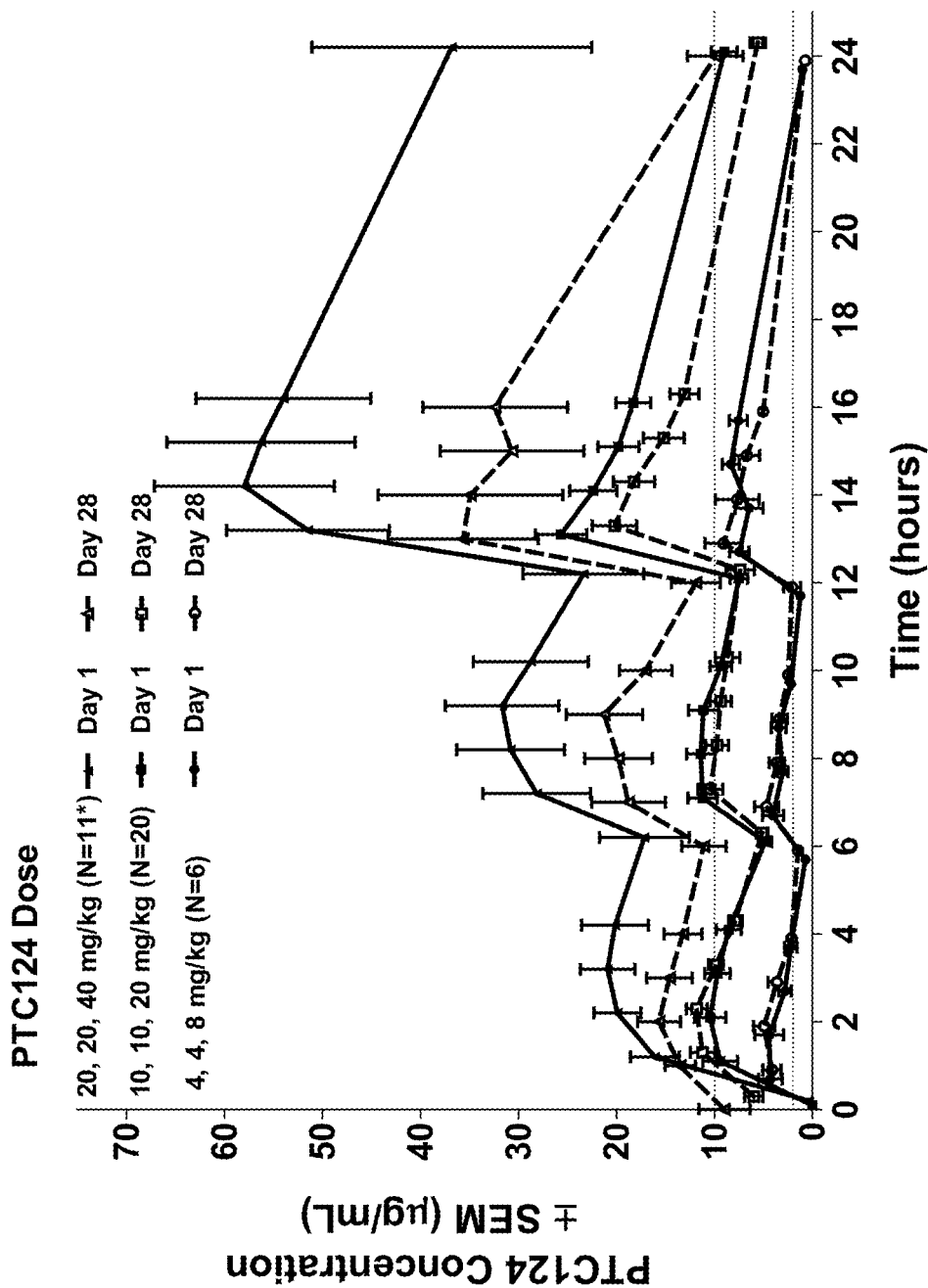

Aurino et al., 2006, "Readthrough strategies for stop codons in Duchenne muscular dystrophy," *Acta Myologica* XXV:5 -12.
Barton et al., 2005, PTC124 nonsense mutation suppression therapy of Duchenne muscular dystrophy, Neurology, 2005;64(suppl 1):A176 (#060).
Clinicaltrials.gov (NCT00234663) (Oct. 6, 2005).
Clinicaltrials.gov (NCT00264888) (Dec. 12, 2005).
Clinicaltrials.gov (NCT00264888) (Dec. 18, 2006).
Drugs of the Future, 2005, vol. 30(1), pp. 94-95.
Du et al., 2008, "PTC124 is an orally bioavailable compound that promotes suppression of the human CFTR-G542X nonsense allele in a CF mouse model." *PNAS* 105(6):2064-2069.
Final Rejection dated Oct. 20, 2011 in connection with U.S. Appl. No. 11/918,114.
Hirawat et al., 2005, Phase 1 Multiple-Dose Safety and PK Study of PTC124 for Nonsense Mutation Suppression Therapy of Duchenne Muscular Dystrophy (DMD), Neurology, 2005;64(suppl 1):A176 (#061).
Hirawat et al., 2007, "Safety, Tolerability, and Pharmacokinetics of PTC124, a Nonaminoglycoside Nonsense Mutation Suppressor, Following Single- and Multiple-Dose Administration to Healthy Male and Female Adult Volunteers," *Journal of Clinical Pharmacology* 47(4):430-444.
Inui et al., 1996, "Gene therapy in Duchenne muscular dystrophy," Brain and Development, 1996, 357-361, 18.5.
Kerem et al., 2008, "Effectiveness of PTC124 treatment of cystic fibrosis caused by nonsense mutations: a prospective phase II trial," *The Lancet* 372:719-27.
Knapman, 2000, "Polymorphic predictions—Understanding the nature of crystalline compounds can be critical in drug development and manufacture," Modern Discovery, Mar. 2000, pp. 53-57.
McElroy et al., 2013, "A Lack of Premature Termination Codon Read-Through Efficacy of PTC124 (Ataluren) in a Diverse Array of Reporter Assays," PLOS Biology 11(6): 1-8.
Non-Final Rejection dated Nov. 23, 2012 in connection with U.S. Appl. No. 11/918,114.
Non-Final Rejection dated Feb. 16, 2011 in connection with U.S. Appl. No. 11/918,114.
Notice of Allowance dated Dec. 19, 2013 in connection with U.S. Appl. No. 11/918,114.
Response to Office Action filed Oct. 29, 2013 in connection with U.S. Appl. No. 11/918,114.
Supplemental Information Methods from Auld et al., 2009, "Mechanism of PTC124 activity in cell based luciferase assays of nonsense codon suppression," *PNAS Early Edition*:1-6 (pp. 1-17).
Supplementary Information from Welch et al., 2007, "PTC124 Targets Genetic Disorders Caused by Nonsense Mutations," *Nature* 447:87-91 (pp. 1-23).
Welch et al., 2005, Characterization of PTC124 activity, specificity, and mechanism of action for nonsense mutation suppression, Neurology, 64(suppl 1):A175 (#059).
Welch et al., 2007, "PTC124 Targets Genetic Disorders Caused by Nonsense Mutations," *Nature* 447:87-91.
Clinicaltrials.gov (NCT00237380) (Oct. 5, 2005).
Hirawat et al., 2005, "Phase 1 Multiple-Dose Safety and PK Study of PTC124 for Nonsense Mutation Suppression Therapy of Duchenne Muscular Dystrophy", 5th Aim Congress, Italian Association for Myology, p. 106.
Singh et al. (1998) "Truncation mutations in the transactivation region of PAX6 result in dominant-negative mutants," *Journal of Biological Chemistry*, 273.34 (1998): 21531-21541.
Ferrari, Stefano, et al., (2011) "Retinitis pigmentosa: genes and disease mechanisms," Current genomics 12.4 (2011): 238-249.

SEM = standard error of mean.

US 10,849,885 B2

METHODS FOR DOSING AN ORALLY ACTIVE 1,2,4-OXADIAZOLE FOR NONSENSE MUTATION SUPPRESSION THERAPY

This application is a continuation of U.S. Non-Provisional application Ser. No. 15/875,296, filed Jan. 19, 2018, currently allowed, which is a continuation of U.S. Non-Provisional application Ser. No. 15/643,724, filed Jul. 7, 2017, issued as U.S. Pat. No. 9,877,952, which is a continuation of U.S. Non-Provisional application Ser. No. 15/345,748, filed Nov. 8, 2016, issued as U.S. Pat. No. 9,737,513, which is a continuation of U.S. Non-Provisional application Ser. No. 14/972,269, filed Dec. 17, 2015, issued as U.S. Pat. No. 9,522,137, which is a continuation of U.S. Non-Provisional application Ser. No. 11/974,068, filed Oct. 11, 2007, issued as U.S. Pat. No. 9,226,919, which claims the benefit of U.S. Provisional Application No. 60/851,450, filed Oct. 12, 2006, each of which is incorporated by reference herein in its entirety.

1. FIELD OF THE INVENTION

The present invention relates to specific doses of, and dosing regimens for, using a 1,2,4-oxadiazole benzoic acid compound in treating or preventing diseases associated with nonsense mutations. In particular, the invention relates to specific doses and dosing regimens for the use of 3-[5-(2-fluoro-phenyl)-[1,2,4]oxadiazol-3-yl]-benzoic acid in mammals having diseases associated with nonsense mutations.

2. BACKGROUND OF THE INVENTION

A new class of 1,2,4-oxadiazole compounds and their use to treat, prevent or manage diseases ameliorated by modulation of premature translation termination or nonsense-mediated mRNA decay is described in U.S. Pat. No. 6,992,096 B1, issued Jan. 31, 2006, entitled "1,2,4-Oxadiazole Benzoic Acid Compounds and Their Use For Nonsense Suppression and the Treatment of Disease," which is incorporated herein by reference in its entirety. One such compound is 3-[5-(2-fluoro-phenyl)-[1,2,4]oxadiazol-3-yl]-benzoic acid. As with all drugs, proper doses and dosing regimens for treating patients having diseases such as Cystic Fibrosis and Duchenne Muscular Dystrophy are essential for achieving a desired or optimal therapeutic effect without adverse or unwanted effects.

Therefore, a need exists for safe, effective, and non-toxic doses and dosing regimens that either prevent or reduce any adverse or unwanted effects or provide an optimal therapeutic effect or both, that is, provide a desirable therapeutic profile.

3. SUMMARY OF THE INVENTION

The invention encompasses dosing regimens wherein specific doses of 3-[5-(2-fluoro-phenyl)-[1,2,4]oxadiazol-3-yl]-benzoic acid or a pharmaceutically acceptable salt, solvate or hydrate thereof are administered at specific time intervals to modulate premature translation termination or nonsense-mediated mRNA decay, or ameliorate one or more symptoms associated therewith, while reducing or avoiding adverse effects or unwanted effects. The invention further encompasses specific doses and unit dosage forms of 3-[5-(2-fluoro-phenyl)-[1,2,4]oxadiazol-3-yl]-benzoic acid or a pharmaceutically acceptable salt, solvate or hydrate thereof.

In one embodiment, the invention relates to methods for administering to a patient in need thereof an effective amount of 3-[5-(2-fluoro-phenyl)-[1,2,4]oxadiazol-3-yl]-benzoic acid or a pharmaceutically acceptable salt, solvate or hydrate thereof one, two or three times in the course of a 24 hour period. The invention also relates to methods for administering to a patient in need thereof a pharmaceutical composition comprising an effective amount of 3-[5-(2-fluoro-phenyl)-[1,2,4]oxadiazol-3-yl]-benzoic acid or a pharmaceutically acceptable salt, solvate or hydrate thereof one, two or three times in the course of a 24 hour period. The dose at each administration during a 24 hour period can be the same or different. In one embodiment, when administered three times in a 24 hour period, the dose at the first two administrations is the same and the third dose is twice the first dose. In another embodiment, all three doses are the same.

In another embodiment, the invention relates to methods for treating, preventing or managing a disease ameliorated by modulation of premature translation termination or nonsense-mediated mRNA decay comprising administering to a patient in need thereof an effective amount of 3-[5-(2-fluoro-phenyl)-[1,2,4]oxadiazol-3-yl]-benzoic acid or a pharmaceutically acceptable salt, solvate or hydrate thereof one, two or three times in the course of a 24 hour period. Preferably, the administration is made three times per day continuously, or with a rest period, for a number of days, weeks, months or years.

The invention also relates to methods for treating, preventing or managing a disease ameliorated by modulation of premature translation termination or nonsense-mediated mRNA decay comprising administering to a patient in need thereof a pharmaceutical composition comprising an effective amount of 3-[5-(2-fluoro-phenyl)-[1,2,4]oxadiazol-3-yl]-benzoic acid or a pharmaceutically acceptable salt, solvate or hydrate thereof one, two or three times in the course of a 24 hour period. Preferably, the administration is made three times per day continuously, or with a rest period, for a number of days, weeks, months or years.

In one embodiment, the invention relates to a method of treating, preventing or reducing cough, comprising administering an effective amount of 3-[5-(2-fluoro-phenyl)-[1,2,4]oxadiazol-3-yl]-benzoic acid or a pharmaceutically acceptable salt, solvate or hydrate thereof to a patient in need thereof.

In one embodiment, the invention relates to a method of increasing dystrophin expression in muscle, comprising administering an effective amount of 3-[5-(2-fluoro-phenyl)-[1,2,4]oxadiazol-3-yl]-benzoic acid or a pharmaceutically acceptable salt, solvate or hydrate thereof to a patient in need thereof.

In one embodiment, the invention relates to a method of administering 3-[5-(2-fluoro-phenyl)-[1,2,4]oxadiazol-3-yl]-benzoic acid or a pharmaceutically acceptable salt, solvate or hydrate thereof wherein the active agent is administered to a patient in need thereof one, two or three times in a 24 hour period, wherein each administration is preferably separated by about 4-14 hours. In a particular embodiment, the dose of active agent is escalated from the first to third dose.

In another embodiment, the invention relates to continuous therapy wherein 3-[5-(2-fluoro-phenyl)-[1,2,4]oxadiazol-3-yl]-benzoic acid or a pharmaceutically acceptable salt, solvate or hydrate thereof is administered to a patient in need thereof for a certain period of time (e.g., 5, 7, 10, 14, 20, 24, 28, 60 or 120 days or longer).

In another embodiment, the invention relates to the administration of 3-[5-(2-fluoro-phenyl)-[1,2,4]oxadiazol-3-yl]-benzoic acid or a pharmaceutically acceptable salt, solvate or hydrate thereof in single or divided (e.g., three times daily) doses between 0.1 mg/kg and 500 mg/kg, 1 mg/kg and 250 mg/kg, 1 mg/kg and 150 mg/kg, 1 mg/kg and 100 mg/kg, 1 mg/kg and 50 mg/kg, 1 mg/kg and 25 mg/kg, 1 mg/kg and 10 mg/kg or 2 mg/kg and 10 mg/kg to a patent in need thereof. In a particular embodiment, 3-[5-(2-fluoro-phenyl)-[1,2,4]oxadiazol-3-yl]-benzoic acid or a pharmaceutically acceptable salt, solvate or hydrate thereof is administered in a dose of about 4 mg/kg, about 7 mg/kg, about 8 mg/kg, about 10 mg/kg, about 14 mg/kg or about 20 mg/kg. In another embodiment, any dose of the 3-[5-(2-fluoro-phenyl)-[1,2,4]oxadiazol-3-yl]-benzoic acid or a pharmaceutically acceptable salt, solvate or hydrate described in the preceding embodiment is administered one, two or three times in a 24 hour period.

In another embodiment, the invention relates to unit dosage formulations that comprise between about 35 mg and about 1400 mg, about 125 mg and about 1000 mg, about 250 mg and about 1000 mg, or about 500 mg and about 1000 mg of 3-[5-(2-fluoro-phenyl)-[1,2,4]oxadiazol-3-yl]-benzoic acid or a pharmaceutically acceptable salt, solvate or hydrate thereof.

In another embodiment, the invention relates to unit dosage formulations that comprise 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of 3-[5-(2-fluoro-phenyl)-[1,2,4]oxadiazol-3-yl]-benzoic acid or a pharmaceutically acceptable salt, solvate or hydrate thereof. In a preferred embodiment, the invention relates to unit dosage formulations that comprise 125 mg, 250 mg or 1000 mg of 3-[5-(2-fluoro-phenyl)-[1,2,4]oxadiazol-3-yl]-benzoic acid or a pharmaceutically acceptable salt, solvate or hydrate thereof.

In another embodiment, the invention relates to a method of maintaining a plasma concentration of 3-[5-(2-fluoro-phenyl)-[1,2,4]oxadiazol-3-yl]-benzoic acid or a pharmaceutically acceptable salt, solvate or hydrate thereof of greater than about 0.1 µg/ml, 0.5 µg/ml, 1 µg/ml, 2 µg/ml, about 5 µg/ml, about 10 µg/ml, about 20 µg/ml, about 25 µg/ml, about 40 µg/ml, about 50 µg/ml, 100 µg/ml, 200 µg/ml, 300 µg/ml, 400 µg/ml, or 500 µg/ml in a patient for at least about 1, 1.5, 2, 2.5, 3, 3.5, 4, 4.5, 5, 6, 8, 12 or 24 hours or longer, comprising administering an effective amount 3-[5-(2-fluoro-phenyl)-[1,2,4]oxadiazol-3-yl]-benzoic acid or a pharmaceutically acceptable salt, solvate or hydrate thereof to a patient in need thereof.

4. DETAILED DESCRIPTION

4.1 Brief Description of the Drawings

FIG. 1 provides the plasma 3-[5-(2-fluoro-phenyl)-[1,2,4]oxadiazol-3-yl]-benzoic acid concentration-time profiles and PK paramaters from 37 of 38 patients in a Phase 2 Duchenne muscular dystrophy study at 4-, 4-, and 8-mg/kg; 10-, 10-, and 20-mg/kg; and 20-, 20- and 40-mg/kg dose levels. The data from one patient was excluded from analysis due to insufficient data.

Figure 2:
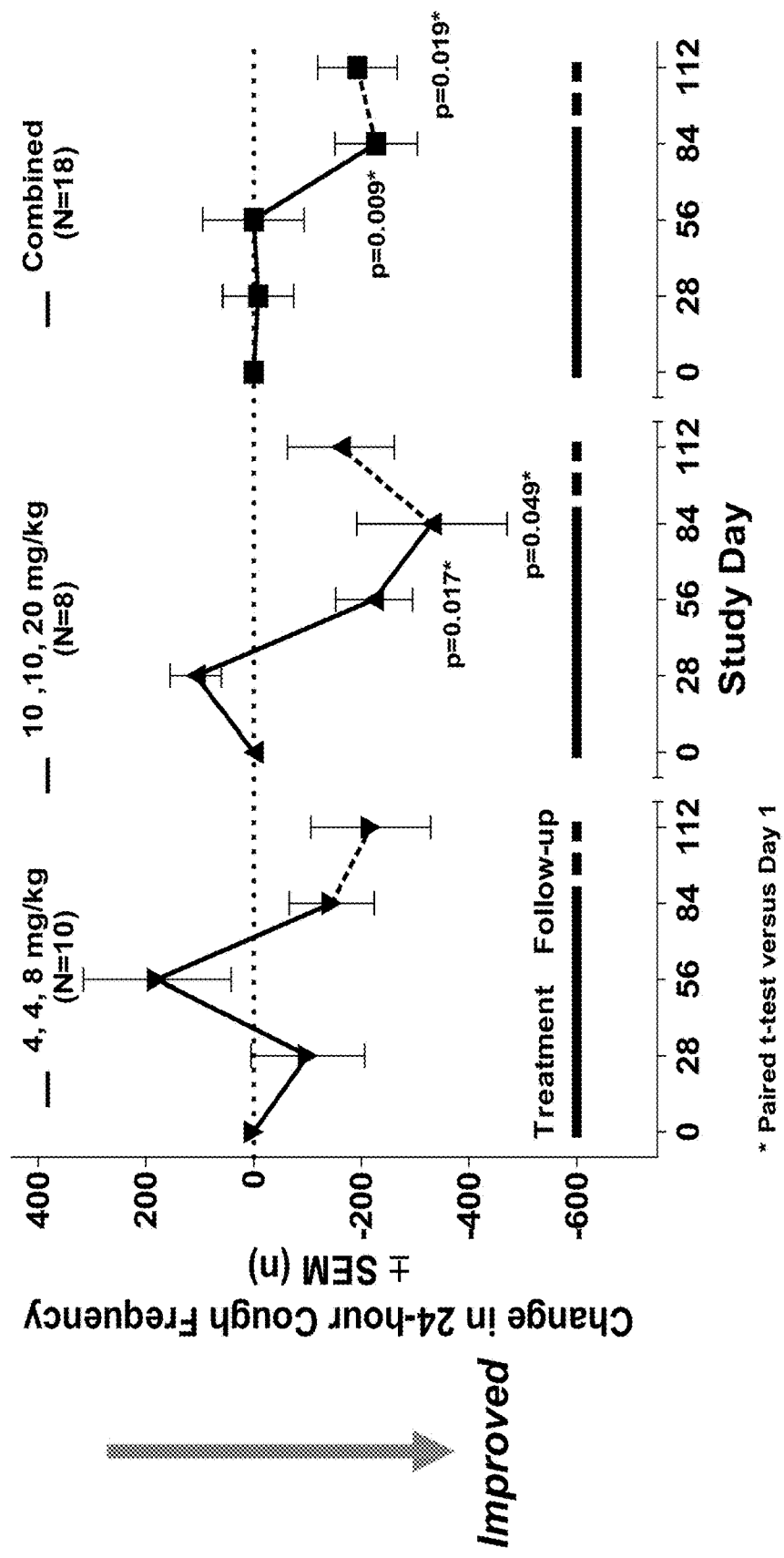

FIG. 2 provides the effect on mean cough frequency over 24 hours by the administration of 3-[5-(2-fluoro-phenyl)-[1,2,4]oxadiazol-3-yl]-benzoic acid to a subject. This data indicates that the administration of 3-[5-(2-fluoro-phenyl)-[1,2,4]oxadiazol-3-yl]-benzoic acid provides an initial improvement in mean cough frequency, followed by temporary increase in mean cough frequency, followed by an overall improvement in mean cough frequency.

4.2 Definitions

As used herein, "premature translation termination" refers to the result of a mutation that changes a codon corresponding to an amino acid to a stop codon.

As used herein, "nonsense-mediated mRNA decay" refers to any mechanism that mediates the decay of mRNAs containing a premature translation termination codon. In a particular embodiment, the nonsense-mediated mRNA decay results from a nonsense mutation of DNA.

As used herein, a "premature termination codon" or "premature stop codon" refers to the occurrence of a stop codon where a codon corresponding to an amino acid should be.

As used herein, a "nonsense mutation" is a point mutation changing a codon corresponding to an amino acid to a stop codon. In a particular embodiment, the nonsense mutation is a mutation that occurs in DNA and is then transcribed into mRNA.

As used herein, "nonsense suppression" refers to the inhibition or suppression of premature translation termination and/or nonsense-mediated mRNA decay. In a particular embodiment, the mRNA decay results from a nonsense mutation of DNA.

As used herein, "modulation of premature translation termination and/or nonsense-mediated mRNA decay" refers to the regulation of gene expression by altering the level of nonsense suppression. For example, if it is desirable to increase production of a defective protein encoded by a gene with a premature stop codon, i.e., to permit readthrough of the premature stop codon of the disease gene so translation of the gene can occur, then modulation of premature translation termination and/or nonsense-mediated mRNA decay entails up-regulation of nonsense suppression.

As used herein, the terms "adverse effect(s)" or "side effect(s)" include, but are not limited to, nausea, vomiting, diarrhea, headache, elevated serum alanine aminotransferase (ALT), elevated serum aspartate aminotransferase (AST), dizziness, elevated serum creatine kinase (CK), abdominal pain, abdominal gas, eye pain, eye swelling, eye burning, nipple sensitivity, breast tenderness, musculoskeletal chest pain, rash, itching, painful submaxillary lymph node, elevated serum lactate dehydrogenase (LDH), elevated serum aldolase and elevated serum triglycerides.

As used herein, the terms "active agent," "drug," and "drug substance" refer to 3-[5-(2-fluoro-phenyl)-[1,2,4]oxadiazol-3-yl]-benzoic acid or a pharmaceutically acceptable salt, solvate or hydrate thereof.

As used herein, the term "dose(s)" means a quantity of active agent to be administered at one time.

As used herein, the term "unit dosage form(s)" includes tablets; caplets; capsules, such as soft elastic gelatin capsules; sachets; cachets; troches; lozenges; dispersions; powders; solutions; gels; liquid dosage forms suitable for oral or mucosal administration to a patient, including suspensions (e.g., aqueous or non-aqueous liquid suspensions), emulsions (e.g., oil-in-water emulsions, or a water-in-oil liquid emulsion), solutions, and elixirs; and sterile solids (e.g., crystalline or amorphous solids) that can be reconstituted to provide liquid dosage forms suitable for oral or parenteral administration to a patient. The unit dosage form does not necessarily have to be administered as a single dose.

As used herein, the terms "dosing regimen" and "dosage(s)" mean the amount of active agent given per time unit and the duration of administration.

As used herein, the term "patient" means an animal (e.g., cow, horse, sheep, pig, chicken, turkey, quail, cat, dog, mouse, rat, rabbit, guinea pig, etc.), preferably a mammal such as a non-primate and a primate (e.g., monkey and human), most preferably a human. In certain embodiments, the patient is a fetus, embryo, infant, child, adolescent or adult. In one embodiment, it has been determined through pre-screening that the patient possesses a nonsense mutation. In another embodiment, it has been determined through pre-screening which nonsense mutation the patient has (i.e., UAA, UGA, or UAG).

As used herein, an "effective amount" refers to that amount of 3-[5-(2-fluoro-phenyl)-[1,2,4]oxadiazol-3-yl]-benzoic acid or a pharmaceutically acceptable salt, solvate or hydrate thereof sufficient to provide a therapeutic benefit in the treatment or management of the disease or to delay or minimize symptoms associated with the disease. In one embodiment, the term "effective amount" refers to the amount of 3-[5-(2-fluoro-phenyl)-[1,2,4]oxadiazol-3-yl]-benzoic acid or a pharmaceutically acceptable salt, solvate or hydrate thereof sufficient to achieve a desired plasma level for a certain duration of time. Preferred effective amounts are specifically described herein.

As used herein, the terms "manage", "managing" and "management" refer to the beneficial effects that a patient derives from the administration of 3-[5-(2-fluoro-phenyl)-[1,2,4]oxadiazol-3-yl]-benzoic acid or a pharmaceutically acceptable salt, solvate or hydrate thereof, which does not result in a cure of the disease.

As used herein, the terms "prevent", "preventing" and "prevention" refer to the prevention of the onset, recurrence, spread or worsening of the disease or a symptom thereof in a patient resulting from the administration of 3-[5-(2-fluoro-phenyl)-[1,2,4]oxadiazol-3-yl]-benzoic acid or a pharmaceutically acceptable salt, solvate or hydrate thereof. Because diseases associated with a nonsense mutation can be genetic, a patient can be screened for the presence of a nonsense mutation. In the case where it is determined through screening that a patient has a nonsense mutation, an effective amount of 3-[5-(2-fluoro-phenyl)-[1,2,4]oxadiazol-3-yl]-benzoic acid or a pharmaceutically acceptable salt, solvate or hydrate thereof can be administered to the patient to prevent the onset, recurrence, spread or worsening of the disease or a symptom thereof.

As used herein, the terms "treat", "treating" and "treatment" refer to the eradication or amelioration of the disease or symptoms associated with the disease. In certain embodiments, such terms refer to minimizing the spread or worsening of the disease resulting from the administration of 3-[5-(2-fluoro-phenyl)-[1,2,4]oxadiazol-3-yl]-benzoic acid or a pharmaceutically acceptable salt, solvate or hydrate thereof to a patient with such a disease.

As used herein, the term "pharmaceutically acceptable salts" refer to salts prepared from pharmaceutically acceptable non-toxic acids or bases including inorganic acids and bases and organic acids and bases. Suitable pharmaceutically acceptable base addition salts for 3-[5-(2-fluoro-phenyl)-[1,2,4]oxadiazol-3-yl]-benzoic acid include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Other examples of salts are well known in the art, see, e.g., Remington's Pharmaceutical Sciences, 18th ed., Mack Publishing, Easton Pa. (1990).

As used herein, the term "hydrate" means 3-[5-(2-fluoro-phenyl)-[1,2,4]oxadiazol-3-yl]-benzoic acid or a pharmaceutically acceptable salt thereof, that further includes a stoichiometric or non-stoichiometric amount of water bound by non-covalent intermolecular forces.

As used herein, the term "solvate" means 3-[5-(2-fluoro-phenyl)-[1,2,4]oxadiazol-3-yl]-benzoic acid or a pharmaceutically acceptable salt thereof, that further includes a stoichiometric or non-stoichiometric amount of a solvent bound by non-covalent intermolecular forces.

4.3 Diseases Associated with Premature Translation Termination

The invention encompasses methods of treating, preventing or managing diseases or disorders ameliorated by the suppression of premature translation termination and/or nonsense-mediated mRNA decay in a patient which comprise administering to a patient in need thereof an effective amount of an orally bioavailable compound (i.e., 3-[5-(2-fluoro-phenyl)-[1,2,4]oxadiazol-3-yl]-benzoic acid or a pharmaceutically acceptable salt, solvate or hydrate thereof) according to the dosages and/or dosing regimens described herein.

In one embodiment, the present invention encompasses the treatment, prevention or management of any disease that is associated with a gene exhibiting premature translation termination and/or nonsense-mediated mRNA decay. In one embodiment, the disease is due, in part, to the lack of expression of the gene resulting from a premature stop codon. Specific examples of genes which may exhibit premature translation termination and/or nonsense-mediated mRNA decay and diseases associated with premature translation termination and/or nonsense-mediated mRNA decay are found in U.S. Patent Application No. 60/390,747, titled: Methods For Identifying Small Molecules That Modulate Premature Translation Termination And Nonsense Mediated mRNA Decay, filed Jun. 21, 2002, which is incorporated herein by reference in its entirety.

In a specific embodiment, the methods, compositions, doses, unit dosage forms and dosing regimens provided herein are useful for the treatment, prevention or management of a disease associated with a nonsense mutation in a gene in an embryo or fetus who has or is predisposed or susceptible to a disease associated with a nonsense mutation in a gene, such as those described herein. In accordance with this embodiment, a pregnant female is administered an effective amount of 3-[5-(2-fluoro-phenyl)-[1,2,4]oxadiazol-3-yl]-benzoic acid or a pharmaceutically acceptable salt, solvate or hydrate thereof which passes through the placenta to the embryo or fetus. In a particular embodiment, an effective amount of 3-[5-(2-fluoro-phenyl)-[1,2,4]oxadiazol-3-yl]-benzoic acid or a pharmaceutically acceptable salt, solvate or hydrate thereof is administered orally to the pregnant female.

Diseases or disorders associated with or ameliorated by the suppression of premature translation termination and/or nonsense-mediated mRNA decay include, but are not limited to: a genetic disease, cancer, an autoimmune disease, a blood disease, a collagen disease, diabetes, a neurodegenerative disease, a proliferative disease, a cardiovascular disease, a pulmonary disease, an inflammatory disease or central nervous system disease.

Specific genetic diseases within the scope of the methods of the invention include, but are not limited to, multiple endocrine neoplasia (type 1, 2 and 3), amyloidosis, mucopolysaccharidosis (type I and III), congenital adrenal hypoplasia, adenomatous polyposis coli, Von Hippel Landau Disease, Menkes Syndrome, hemophilia A, hemophilia B, collagen VII, Alagille Syndrome, Townes-Brocks Syndrome, rhabdoid tumor, epidermolysis bullosa, Hurler's Syndrome, Coffin-Lowry Syndrome, aniridia, Charcot-Maria-Tooth Disease, myotubular myopathy, X-linked myotubular myopathy, X-linked chondrodysplasia, X-linked agammaglobulinemia, polycystic kidney disease, spinal muscular atrophy, familial adenomatous poliposis, pyruvate dehydrogenase deficiency, phenylketonuria, neurofibromatosis 1, neurofibromatosis 2, Alzheimer's disease, Tay Sachs disease, Rett Syndrome, Hermansky-Pudlak Syndrome, ectodermal dysplasia/skin fragility syndrome, Leri-Weill dyschondrosteosis, rickets, hypophosphataemic, adrenoleukodystrophy, gyrate atrophy, atherosclerosis, sensorineural deafness, dystonia, Dent Disease, acute intermittent porphyria, Cowden Disease, Herlitz epidermolysis bullosa, Wilson Disease, Treacher-Collins Syndrome, pyruvate kinase deficiency, giantism, dwarfism, hypothyroidism, hyperthyroidism, aging, obesity, Parkinson's disease, Niemann Pick's disease C, Cystic Fibrosis, muscular dystrophy, heart disease, kidney stones, ataxia-telangiectasia, familial hypercholesterolemia, retinitis pigmentosa, lysosomal storage disease, tuberous sclerosis, Duchenne Muscular Dystrophy, and Marfan Syndrome.

In another embodiment, the genetic disease is an autoimmune disease. In a preferred embodiment, the autoimmune disease is rheumatoid arthritis or graft versus host disease.

In another embodiment, the genetic disease is a blood disease. In a preferred embodiment, the blood disease is hemophilia A, Von Willebrand disease (type 3), ataxia-telangiectasia, b-thalassemia or kidney stones.

In another embodiment, the genetic disease is a collagen disease. In a embodiment, the collagen disease is osteogenesis imperfecta or cirrhosis.

In another embodiment, the genetic disease is diabetes.

In another embodiment, the genetic disease is an inflammatory disease. In a preferred embodiment, the inflammatory disease is arthritis.

In another embodiment, the genetic disease is a central nervous system disease. In one embodiment the central nervous system disease is a neurodegenerative disease. In a preferred embodiment, the central nervous system disease is multiple sclerosis, muscular dystrophy, Duchenne muscular dystrophy, Alzheimer's disease, Tay Sachs disease, late infantile neuronal ceroid lipofuscinosis (LINCL) or Parkinson's disease.

In another embodiment, the genetic disease is cancer. In a preferred embodiment, the cancer is of the head and neck, eye, skin, mouth, throat, esophagus, chest, bone, lung, colon, sigmoid, rectum, stomach, prostate, breast, ovaries, kidney, liver, pancreas, brain, intestine, heart or adrenals. The cancer can be primary or metastatic. Cancers include solid tumors, hematological cancers and other neoplasias.

In another preferred embodiment, the cancer is associated with tumor suppressor genes (see e.g. Garinis et al. 2002, Hum Gen 111:115-117; Meyers et al. 1998, Proc. Natl. Acad. Sci. USA, 95: 15587-15591; Kung et al. 2000, Nature Medicine 6(12): 1335-1340. Such tumor suppressor genes include, but are not limited to, APC, ATM, BRAC1, BRAC2, MSH1, pTEN, Rb, CDKN2, NF1, NF2, WT1, and p53.

In a particularly preferred embodiment, the tumor suppressor gene is the p53 gene. Nonsense mutations have been identified in the p53 gene and have been implicated in cancer. Several nonsense mutations in the p53 gene have been identified (see, e.g., Masuda et al., 2000, Tokai J Exp Clin Med. 25(2):69-77; Oh et al., 2000, Mol Cells 10(3): 275-80; Li et al., 2000, Lab Invest. 80(4):493-9; Yang et al., 1999, Zhonghua Zhong Liu Za Zhi 21(2):114-8; Finkelstein et al., 1998, Mol Diagn. 3(1):37-41; Kajiyama et al., 1998, Dis Esophagus. 11(4):279-83; Kawamura et al., 1999, Leuk Res. 23(2):115-26; Radig et al., 1998, Hum Pathol. 29(11): 1310-6; Schuyer et al., 1998, Int J Cancer 76(3):299-303; Wang-Gohrke et al., 1998, Oncol Rep. 5(1):65-8; Fulop et al., 1998, J Reprod Med. 43(2):119-27; Ninomiya et al., 1997, J Dermatol Sci. 14(3):173-8; Hsieh et al., 1996, Cancer Lett. 100(1-2):107-13; Rall et al., 1996, Pancreas. 12(1):10-7; Fukutomi et al., 1995, Nippon Rinsho. 53(11): 2764-8; Frebourg et al., 1995, Am J Hum Genet. 56(3):608-15; Dove et al., 1995, Cancer Surv. 25:335-55; Adamson et al., 1995, Br J Haematol. 89(1):61-6; Grayson et al., 1994, Am J Pediatr Hematol Oncol. 16(4):341-7; Lepelley et al., 1994, Leukemia. 8(8):1342-9; McIntyre et al., 1994, J Clin Oncol. 12(5):925-30; Horio et al., 1994, Oncogene. 9(4): 1231-5; Nakamura et al., 1992, Jpn J Cancer Res. 83(12): 1293-8; Davidoff et al., 1992, Oncogene. 7(1):127-33; and Ishioka et al., 1991, Biochem Biophys Res Commun. 177 (3):901-6; the disclosures of which are hereby incorporated by reference in their entireties).

In other embodiments, diseases to be treated, prevented or managed by administering to a patient in need thereof an effective amount of a 3-[5-(2-fluoro-phenyl)-[1,2,4]oxadiazol-3-yl]-benzoic acid or a pharmaceutically acceptable salt, solvate or hydrate thereof include, but are not limited to, solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia, chronic lymphocytic leukemia, hairy cell leukemia, or multiple myeloma. See e.g., *Harrison's Principles of Internal Medicine*, Eugene Braunwald et al., eds., pp. 491-762 (15th ed. 2001).

In one embodiment, the invention relates to a method of treating, preventing or reducing cough, comprising administering an effective amount of 3-[5-(2-fluoro-phenyl)-[1,2,4]oxadiazol-3-yl]-benzoic acid or a pharmaceutically acceptable salt, solvate or hydrate thereof to a patient in need thereof. In a particular embodiment, the patient has cystic fibrosis. In another embodiment, the cough is chronic cough. In another embodiment, 3-[5-(2-fluoro-phenyl)-[1,2,4]oxadiazol-3-yl]-benzoic acid or a pharmaceutically acceptable salt, solvate or hydrate thereof is administered as a dosage form provided herein or according to a dosing regimen provided herein.

In one embodiment, the invention relates to a method of increasing dystrophin expression in muscle, comprising administering an effective amount of 3-[5-(2-fluoro-phenyl)-[1,2,4]oxadiazol-3-yl]-benzoic acid or a pharmaceutically acceptable salt, solvate or hydrate thereof to a patient in need thereof. In a particular embodiment, the invention relates to a method of increasing dystrophin expression in muscle cells, comprising contacting the muscle cells with an effective amount of 3-[5-(2-fluoro-phenyl)-[1,2,4]oxadiazol-3-yl]-benzoic acid or a pharmaceutically acceptable salt, solvate or hydrate thereof. In one embodiment, the muscle cells are contacted in vitro. In a specific embodiment, the patient has Duchenne muscular dystrophy. In another embodiment, 3-[5-(2-fluoro-phenyl)-[1,2,4]oxadiazol-3-yl]-benzoic acid or a pharmaceutically acceptable salt, solvate or hydrate thereof is administered as a dosage form provided herein or according to a dosing regimen provided herein.

4.4 Doses and Dosing Regimens

Without being limited by theory, the present invention encompasses, in part, specific doses and dosing regimens for 3-[5-(2-fluoro-phenyl)-[1,2,4]oxadiazol-3-yl]-benzoic acid or a pharmaceutically acceptable salt, solvate or hydrate thereof that optimize the suppression of premature translation termination and/or nonsense-mediated mRNA decay. In a preferred embodiment, the nonsense-mediated mRNA decay results from a nonsense mutation of DNA.

The novel methods of the invention encompass the treatment, prevention and management of diseases treatable or preventable by the suppression of premature translation termination and/or nonsense-mediated mRNA decay or symptoms thereof while reducing or avoiding adverse or unwanted effects, e.g., toxicities or side effects. The preferred route of administration for the doses and dosing regimens described herein is oral (i.e., ingestion of a solution, a colloid solution or a solution with additional active agent, above the saturating concentration of active agent).

The doses and dosing regimens described herein are thought to be useful due to their ability to achieve and maintain a desirable plasma concentration of the active agent. Without being limited by theory, it is thought that achieving and maintaining a relatively constant plasma concentration of active agent (such as those described in section 4.4) over, for example, a 24 hour period or longer, provides a beneficial therapeutic effect to the patient. The doses and dosing regimens described herein are useful for achieving and maintaining such therapeutic plasma concentrations of active agent.

In one embodiment, the invention relates to a method of administering 3-[5-(2-fluoro-phenyl)-[1,2,4]oxadiazol-3-yl]-benzoic acid or a pharmaceutically acceptable salt, solvate or hydrate thereof wherein the active agent is administered to a patient in need thereof once in a 12 or 24 hour period.

In another embodiment, the invention relates to a method of administering 3-[5-(2-fluoro-phenyl)-[1,2,4]oxadiazol-3-yl]-benzoic acid or a pharmaceutically acceptable salt, solvate or hydrate thereof wherein the active agent is administered to a patient in need thereof two times in a 12 or 24 hour period, wherein each administration is preferably separated by about 4-14 hours, in one embodiment 12 hours. In these embodiments, the active agent can be administered, for example, at meal time, such as breakfast and supper.

In another embodiment, the invention relates to a method of administering 3-[5-(2-fluoro-phenyl)-[1,2,4]oxadiazol-3-yl]-benzoic acid or a pharmaceutically acceptable salt, solvate or hydrate thereof wherein the active agent is administered to a patient in need thereof three times in a 12 or 24 hour period, wherein each administration is preferably separated by about 4-14 hours. In a particular embodiment, the active agent is administered once in the morning, once in the afternoon and once in the evening. Preferred intervals between doses include 4, 5, 6, 7, 8, 9, 10, 11, 12, 13 and 14 hours.

In one embodiment, the dose of active agent is escalated throughout a 24 hour period. In another embodiment, the second dose administered is escalated (e.g., doubled). In another embodiment, the first and second dose administered are kept constant and the third dose administered is escalated (e.g., doubled). In a particular embodiment, the three doses in a 24 hour period are administered according to the formula: 1X, 1X, 2X, where X is a particular initial dose (e.g., 4 mg/kg, 7 mg/kg, 10 mg/kg, 20 mg/kg, 25 mg/kg, 30 mg/kg, 35 mg/kg, 40 mg/kg or 50 mg/kg). In another embodiment, the active agent is administered within (i.e., before or after) about 10, 15, 30, 45 or 60 minutes of the patient having food. In one embodiment, an effective amount of the active agent is sprinkled on or mixed in food. In another embodiment, the active agent is administered without food.

A particularly preferred dosing regimen is that where a patient is administered the active agent within 30 minutes after a meal at approximately 6-, 6-, and 12-hour intervals (e.g., at ~7:00 AM after breakfast, ~1:00 PM after lunch, and at ~7:00 PM after supper).

In yet another embodiment, the invention relates to the administration of 3-[5-(2-fluoro-phenyl)-[1,2,4]oxadiazol-3-yl]-benzoic acid or a pharmaceutically acceptable salt, solvate or hydrate thereof in single or divided (e.g., three times in a 24 hour period) doses between 0.1 mg/kg and 500 mg/kg, 1 mg/kg and 250 mg/kg, 1 mg/kg and 150 mg/kg, 1 mg/kg and 100 mg/kg, 1 mg/kg and 50 mg/kg, 1 mg/kg and 25 mg/kg, 1 mg/kg and 10 mg/kg or 2 mg/kg and 10 mg/kg to a patent in need thereof. In a particular embodiment, 3-[5-(2-fluoro-phenyl)-[1,2,4]oxadiazol-3-yl]-benzoic acid or a pharmaceutically acceptable salt, solvate or hydrate thereof is administered in a dose of about 2-6 mg/kg, about 5-9 mg/kg, about 6-10 mg/kg, about 8-12 mg/kg, about 12-16 mg/kg or about 18-22 mg/kg. In a particular embodiment, 3-[5-(2-fluoro-phenyl)-[1,2,4]oxadiazol-3-yl]-benzoic acid or a pharmaceutically acceptable salt, solvate or hydrate thereof is administered in a dose of about 4 mg/kg, about 7 mg/kg, about 8 mg/kg, about 10 mg/kg, about 14 mg/kg, about 20 mg/kg, about 25 mg/kg, about 30 mg/kg, about 35 mg/kg, about 40 mg/kg or about 50 mg/kg. In another embodiment, any dose of the 3-[5-(2-fluoro-phenyl)-[1,2,4] oxadiazol-3-yl]-benzoic acid or a pharmaceutically acceptable salt, solvate or hydrate described in the preceding embodiment is administered three times in a 24 hour period.

In another embodiment, the invention relates to continuous therapy wherein 3-[5-(2-fluoro-phenyl)-[1,2,4]oxadiazol-3-yl]-benzoic acid or a pharmaceutically acceptable salt, solvate or hydrate thereof is administered daily to a patient in need thereof for a certain period of time (e.g., 5, 7, 10, 14, 20, 24, 28, 60 or 120 days or more). In one embodiment, the active agent is continuously administered three times per 24 hour period. In another embodiment, the active agent is administered continuously daily, weekly, monthly or yearly. In a specific embodiment, the active agent is continuously administered three times per 24 hour period at doses of about 4 mg/kg, about 4 mg/kg and about 8 mg/kg for days, weeks, months or years. In a specific embodiment, the active agent is continuously administered three times per 24 hour period at doses of about 7 mg/kg, about 7 mg/kg and about 14 mg/kg for days, weeks, months or years. In a specific embodiment, the active agent is continuously administered three times per 24 hour period at doses of about 10 mg/kg, about 10 mg/kg and about 20 mg/kg for days, weeks, months or years. In a specific embodiment, the active agent is continuously administered three times per 24 hour period at doses of about 30 mg/kg, about 30 mg/kg and about 60 mg/kg for days, weeks, months or years. In a specific embodiment, the active agent is continuously administered three times per 24 hour period at doses of about 10 mg/kg, about 10 mg/kg and about 20 mg/kg for days, weeks, months or years. In a specific embodiment, the active agent is continuously administered three times per 24 hour period at doses of about 40 mg/kg, about 40 mg/kg and about 80 mg/kg for days, weeks, months or years. In each 24 hour period that the active agent is administered, it is preferably administered three times at approximately 6-, 6, and 12-hour intervals (e.g., at ~7:00 AM after breakfast, ~1:00 PM after lunch, and at ~7:00 PM after supper). Continuous therapy is preferably used for the treatment, prevention or management of Cystic Fibrosis and Duchenne Muscular Dystrophy.

Treatment periods for a course of therapy can span one week, two weeks, three weeks, four weeks, five weeks, six weeks, seven weeks, eight weeks, nine weeks, ten weeks, eleven weeks, twelve weeks, thirteen weeks, fourteen weeks, four months, five months, six months, seven months, eight months, nine months, ten months, eleven months, one year, two years, three years, four years, five years or longer. The treatment periods can be interrupted by periods of rest which can span a day, one week, two weeks, three weeks, four weeks, five weeks, six weeks, seven weeks, eight weeks, nine weeks, ten weeks, eleven weeks, twelve weeks, thirteen weeks, fourteen weeks, four months, five months, six months, seven months, eight months, nine months, ten months, eleven months, one year, two years, three years, four years, five years or longer. Such determinations can be made by one skilled in the art (e.g., a physician).

In a particular embodiment, treatment is continuous for 14 days, followed by no treatment for 14 days, followed by continuous treatment for an additional 14 days. In one embodiment, the dose given during the second 14 days of treatment is greater than that given during the first 14 days of treatment. As a non-limiting example, a patient in need thereof is administered three doses of 3-[5-(2-fluoro-phenyl)-[1,2,4]oxadiazol-3-yl]-benzoic acid or a pharmaceutically acceptable salt, solvate or hydrate thereof (e.g., 4 mg/kg, 4 mg/kg and 8 mg/kg) in a 24 hour period for 14 continuous days, followed by 14 days without treatment, followed by administration of three doses of 3-[5-(2-fluoro-phenyl)-[1,2,4]oxadiazol-3-yl]-benzoic acid or a pharmaceutically acceptable salt, solvate or hydrate thereof (e.g., 10 mg/kg, 10 mg/kg and 20 mg/kg) in a 24 hour period for an additional 14 continuous days.

In another embodiment, treatment is continuous for 28 days. Continuous treatment can be interrupted by one or more days, months, weeks or years. Continuous treatment can also be followed by a rest period lasting one or more days, months, weeks or years, with continuous treatment then resuming after the rest period.

In certain embodiments, 3-[5-(2-fluoro-phenyl)-[1,2,4] oxadiazol-3-yl]-benzoic acid or a pharmaceutically acceptable salt, solvate or hydrate thereof is administered according to the doses and dosing schedules described herein in combination with a second active agent (e.g., simultaneously or sequentially). In particular embodiments, 3-[5-(2-fluoro-phenyl)-[1,2,4]oxadiazol-3-yl]-benzoic acid or a pharmaceutically acceptable salt, solvate or hydrate thereof is administered according to the doses and dosing schedules described herein in combination with an aminoglycoside, a corticosteroid, a pancreatic enzyme, an antibiotic, insulin, a hypoglycemic agent, an omega-3 fatty acid, a chemotherapeutic agent, or an enzyme replacement therapy. The administration of the second active agent can be topical, enteral (e.g. oral, duodenal, rectal), parenteral (e.g., intravenous, intraarterial, intramuscular, subcutaneous, intradermal or interaperitoneal) or intrathecal. In certain embodiments, 3-[5-(2-fluoro-phenyl)-[1,2,4]oxadiazol-3-yl]-benzoic acid or a pharmaceutically acceptable salt, solvate or hydrate thereof is administered according to the doses and dosing schedules described herein in combination with radiation therapy.

It will be understood that the amounts of active agent administered to a patient in need thereof are or can be calculated based upon the actual weight of the patient in question or the average weight of the patient population in question (e.g., white males, white females, African American males, African American females, Asian males or Asian females, including adults and children).

4.5 Plasma Concentrations

In one embodiment, the invention relates to a method of maintaining a plasma concentration of 3-[5-(2-fluoro-phenyl)-[1,2,4]oxadiazol-3-yl]-benzoic acid or a pharmaceutically acceptable salt, solvate or hydrate thereof of greater than: about 0.1 μg/ml, about 0.5 μg/ml, about 2 μg/ml, about 5 μg/ml, about 10 μg/ml, about 20 μg/ml, about 25 μg/ml, about 40 μg/ml, about 50 μg/ml, about 100 μg/ml, about 150 μg/ml, about 200 μg/ml, about 250 μg/ml or about 500 μg/ml in a patient for at least about 2, 2.5, 3, 3.5, 4, 4.5, 5, 6, 8, 12 or 24 hours or longer, comprising administering an effective amount of 3-[5-(2-fluoro-phenyl)-[1,2,4]oxadiazol-3-yl]-benzoic acid or a pharmaceutically acceptable salt, solvate or hydrate thereof to a patient in need thereof. In a particular embodiment, the administration is oral. Levels of 3-[5-(2-fluoro-phenyl)-[1,2,4]oxadiazol-3-yl]-benzoic acid or a pharmaceutically acceptable salt, solvate or hydrate thereof in plasma can be measured, for example, by high performance liquid chromatography (HPLC).

In another embodiment, the invention relates to a method of maintaining a plasma concentration of 3-[5-(2-fluoro-phenyl)-[1,2,4]oxadiazol-3-yl]-benzoic acid or a pharmaceutically acceptable salt, solvate or hydrate thereof of about 0.1 µg/ml to about 500 µg/ml or about 2 µg/ml to about 10 µg/ml in a patient for at least about 2, 2.5, 3, 3.5, 4, 4.5, 5, 6, 8, 12 or 24 hours or longer, comprising administering an effective amount of 3-[5-(2-fluoro-phenyl)-[1,2,4]oxadiazol-3-yl]-benzoic acid or a pharmaceutically acceptable salt, solvate or hydrate thereof to a patient in need thereof one, two or three times per day at the same or escalating doses (e.g., 1X, 1X, 2X as described herein). In a particular embodiment, the administration is oral.

In a particular embodiment, a patient's plasma level of 3-[5-(2-fluoro-phenyl)-[1,2,4]oxadiazol-3-yl]-benzoic acid or a pharmaceutically acceptable salt, solvate or hydrate thereof is maintained above about 2 µg/ml for at least about 2, 2.5, 3, 3.5, 4, 4.5, 5, 6, 8, 12 or 24 hours or longer by administration of the active agent one, two or three times per day to a patient in need thereof. In another embodiment, a patient's plasma level of 3-[5-(2-fluoro-phenyl)-[1,2,4]oxadiazol-3-yl]-benzoic acid or a pharmaceutically acceptable salt, solvate or hydrate thereof is maintained between about 2 µg/ml to about 10 µg/ml for at least about 2, 2.5, 3, 3.5, 4, 4.5, 5, 6, 8, 12 or 24 hours or longer hours by administration of the active agent one, two or three times per day to a patient in need thereof. In a particular embodiment, a patient's plasma level of 3-[5-(2-fluoro-phenyl)-[1,2,4]oxadiazol-3-yl]-benzoic acid or a pharmaceutically acceptable salt, solvate or hydrate thereof is maintained above about 10 µg/ml for at least about 2, 2.5, 3, 3.5, 4, 4.5, 5, 6, 8, 12 or 24 hours or longer by administration of the active agent one, two or three times per day to a patient in need thereof. In a particular embodiment, the administration is oral.

In a particular embodiment, provided herein are methods for achieving a $C_{max}$ of 1 µg/mL to 1000 µg/mL, 1 µg/mL to 750 µg/mL, 1 µg/mL to 500 µg/mL, 1 µg/mL to 400 µg/mL, 1 µg/mL to 300 µg/mL, 1 µg/mL to 250 µg/mL, 1 µg/mL to 200 µg/mL, 1 µg/mL to 150 µg/mL, 1 µg/mL to 100 µg/mL, 1 µg/mL to 50 µg/mL, 1 µg/mL to 40 µg/mL, 1 µg/mL to 30 µg/mL, 1 µg/mL to 20 µg/mL, 1 µg/mL to 10 µg/mL, or 10 µg/mL to 30 µg/mL of 3-[5-(2-fluoro-phenyl)-[1,2,4]oxadiazol-3-yl]-benzoic acid or a pharmaceutically acceptable salt, solvate or hydrate thereof is in a patient comprising administering an effective amount of 3-[5-(2-fluoro-phenyl)-[1,2,4]oxadiazol-3-yl]-benzoic acid or a pharmaceutically acceptable salt, solvate or hydrate thereof one, two or three times per day to a patient in need thereof.

In a particular embodiment, provided herein are methods for achieving a $AUC_{0-24}$ of 50 µg·hour/mL to 1000 µg·hour/mL, 50 µg·hour/mL to 750 µg·hour/mL, 50 µg·hour/mL to 500 µg·hour/mL, 50 µg·hour/mL to 400 µg·hour/mL, 50 µg·hour/mL to 300 µg·hour/mL, 50 µg·hour/mL to 250 µg·hour/mL, 50 µg·hour/mL to 200 µg·hour/mL, 50 µg·hour/mL to 150 µg·hour/mL, or 50 µg·hour/mL to 100 µg·hour/mL of 3-[5-(2-fluoro-phenyl)-[1,2,4]oxadiazol-3-yl]-benzoic acid or a pharmaceutically acceptable salt, solvate or hydrate thereof is in a patient comprising administering an effective amount of 3-[5-(2-fluoro-phenyl)-[1,2,4]oxadiazol-3-yl]-benzoic acid or a pharmaceutically acceptable salt, solvate or hydrate thereof one, two or three times per day to a patient in need thereof.

In another embodiment, the invention relates to a method of administering 3-[5-(2-fluoro-phenyl)-[1,2,4]oxadiazol-3-yl]-benzoic acid or a pharmaceutically acceptable salt, solvate or hydrate thereof to a patient in need thereof that provides an in vivo plasma profile with a 90% confidence interval (CI) for a natural-log transformed ratio within 80% to 125%, 90% to 115% or 95% to 110% for at least one of the following bioavailability parameters for 3-[5-(2-fluoro-phenyl)-[1,2,4]oxadiazol-3-yl]-benzoic acid or a pharmaceutically acceptable salt, solvate or hydrate thereof:

(a) a mean $AUC_{0-24}$ of 87 µg·hour/mL at day 1 of administration or 91 µg·hour/mL at day 28 of administration;

(b) a mean $C_{max}$ of 10 µg/mL at day 1 of administration or 11 µg/mL at day 28 of administration; and (c) a mean $C_{min}$ of 0.5 µg/mL at day 1 of administration or 0.6 µg/mL at day 28 of administration.

In another embodiment, the invention relates to a method of administering 3-[5-(2-fluoro-phenyl)-[1,2,4]oxadiazol-3-yl]-benzoic acid or a pharmaceutically acceptable salt, solvate or hydrate thereof to a patient in need thereof that provides an in vivo plasma profile with a 90% CI for a natural-log transformed ratio within 80% to 125%, 90% to 115% or 95% to 110% for at least one of the following bioavailability parameters for 3-[5-(2-fluoro-phenyl)-[1,2,4]oxadiazol-3-yl]-benzoic acid or a pharmaceutically acceptable salt, solvate or hydrate thereof:

(a) a mean $AUC_{0-24}$ of 291 µg·hour/mL at day 1 of administration or 235 µg·hour/mL at day 28 of administration;

(b) a mean $C_{max}$ of 27 µg/mL at day 1 of administration or 22 µg/mL at day 28 of administration; and (c) a mean $C_{min}$ of 3.8 µg/mL at day 1 of administration or 3.4 µg/mL at day 28 of administration.

In another embodiment, the invention relates to a method of administering 3-[5-(2-fluoro-phenyl)-[1,2,4]oxadiazol-3-yl]-benzoic acid or a pharmaceutically acceptable salt, solvate or hydrate thereof to a patient in need thereof that provides an in vivo plasma profile with a 90% CI for a natural-log transformed ratio within 80% to 125%, 90% to 115% or 95% to 110% for at least one of the following bioavailability parameters for 3-[5-(2-fluoro-phenyl)-[1,2,4]oxadiazol-3-yl]-benzoic acid or a pharmaceutically acceptable salt, solvate or hydrate thereof:

(a) a mean $AUC_{0-24}$ of 866 µg·hour/mL at day 1 of administration or 490 µg·hour/mL at day 28 of administration;

(b) a mean $C_{max}$ of 76 µg/mL at day 1 of administration or 46 µg/mL at day 28 of administration; and (c) a mean $C_{min}$ of 9.6 µg/mL at day 1 of administration or 6.7 µg/mL at day 28 of administration.

4.6 Patient Populations

Particular patient populations which the methods and compositions of the present invention are useful for include adults and children who have or are susceptible to having (e.g., due to environmental or genetic factors) a disease associated with a nonsense mutation, such as those described herein.

In one embodiment, it has been determined through pre-screening that the patient or a relative of the patient has a nonsense mutation (i.e., UAA, UGA, or UAG).

4.7 Pharmaceutical Compositions and Unit Dosage Formulations

Pharmaceutical compositions and single unit dosage forms comprising 3-[5-(2-fluoro-phenyl)-[1,2,4]oxadiazol-3-yl]-benzoic acid or a pharmaceutically acceptable salt, solvate or hydrate thereof are also encompassed by the invention. Individual dosage forms of the invention may be suitable for oral, mucosal (including sublingual, buccal, rectal, nasal, or vaginal) or parenteral (including subcutaneous, intramuscular, bolus injection, intraarterial, or intravenous) administration. Preferred pharmaceutical compositions and single unit dosage forms are suitable for oral administration.

In one embodiment, the pharmaceutical composition is a solid oral dosage form. In one embodiment, the pharmaceutical composition is a liquid oral dosage form. In a particular embodiment, present invention provides doses, unit dosage formulations and pharmaceutical compositions wherein 3-[5-(2-fluoro-phenyl)-[1,2,4]oxadiazol-3-yl]-benzoic acid or a pharmaceutically acceptable salt, solvate or hydrate thereof is orally bioavailable. Advantages of oral administration can include ease of administration, higher patient compliance with the dosing regimen, clinical efficacy, fewer complications, shorter hospital stays, and overall cost savings.

In another embodiment, the invention relates to unit dosage formulations that comprise between about 35 mg and about 1400 mg, about 125 mg and about 1000 mg, about 250 mg and about 1000 mg, or about 500 mg and about 1000 mg of 3-[5-(2-fluoro-phenyl)-[1,2,4]oxadiazol-3-yl]-benzoic acid or a pharmaceutically acceptable salt, solvate or hydrate thereof. In one embodiment, the unit dosage formulation comprises 3-[5-(2-fluoro-phenyl)-[1,2,4]oxadiazol-3-yl]-benzoic acid or a pharmaceutically acceptable salt, solvate or hydrate thereof and one or more carriers or excipients suitable for suspension in a pharmaceutically acceptable solvent (e.g., water, milk, a carbonated beverage, juice, apple sauce, baby food or baby formula) in a bottle.

In another embodiment, the invention relates to unit dosage formulations that comprise 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of 3-[5-(2-fluoro-phenyl)-[1,2,4]oxadiazol-3-yl]-benzoic acid or a pharmaceutically acceptable salt, solvate or hydrate thereof. Preferred unit dosage formulations comprise about 125 mg, about 250 or about 1000 mg of 3-[5-(2-fluoro-phenyl)-[1,2,4]oxadiazol-3-yl]-benzoic acid or a pharmaceutically acceptable salt, solvate or hydrate thereof. In one embodiment, the unit dosage formulation comprises 3-[5-(2-fluoro-phenyl)-[1,2,4]oxadiazol-3-yl]-benzoic acid or a pharmaceutically acceptable salt, solvate or hydrate thereof and one or more carriers or excipients suitable for suspension in a pharmaceutically acceptable solvent (e.g., water, milk, a carbonated beverage, juice, apple sauce, baby food or baby formula) in a bottle. Preferred unit dosage formulations are powders and sachets.

In one embodiment, the invention relates to a solid dosage form comprising 250 mg, 500 mg, 750 mg or 1000 mg of 3-[5-(2-fluoro-phenyl)-[1,2,4]oxadiazol-3-yl]-benzoic acid or a pharmaceutically acceptable salt, solvate or hydrate thereof which when administered to a patient in need thereof in three daily doses of 4 mg/kg, 4 mg/kg and 8 mg/kg, respectively, provides an in vivo plasma profile with a 90% confidence interval (CI) for a natural-log transformed ratio within 80% to 125%, 90% to 115% or 95% to 110% for at least one of the following bioavailability parameters for 3-[5-(2-fluoro-phenyl)-[1,2,4]oxadiazol-3-yl]-benzoic acid or a pharmaceutically acceptable salt, solvate or hydrate thereof:

(a) a mean $AUC_{0-24}$ of 87 µg·hour/mL at day 1 of administration or 91 µg·hour/mL at day 28 of administration;

(b) a mean $C_{max}$ of 10 µg/mL at day 1 of administration or 11 µg/mL at day 28 of administration; and (c) a mean $C_{min}$ of 0.5 µg/mL at day 1 of administration or 0.6 µg/mL at day 28 of administration.

In one embodiment, the invention relates to a solid dosage form comprising 250 mg, 500 mg, 750 mg or 1000 mg of 3-[5-(2-fluoro-phenyl)-[1,2,4]oxadiazol-3-yl]-benzoic acid or a pharmaceutically acceptable salt, solvate or hydrate thereof which when administered to a patient in need thereof in three daily doses of 10 mg/kg, 10 mg/kg and 20 mg/kg, respectively, provides an in vivo plasma profile with a 90% CI for a natural-log transformed ratio within 80% to 125%, 90% to 115% or 95% to 110% for at least one of the following bioavailability parameters for 3-[5-(2-fluoro-phenyl)-[1,2,4]oxadiazol-3-yl]-benzoic acid or a pharmaceutically acceptable salt, solvate or hydrate thereof:

(a) a mean $AUC_{0-24}$ of 291 µg·hour/mL at day 1 of administration or 235 µg·hour/mL at day 28 of administration;

(b) a mean $C_{max}$ of 27 µg/mL at day 1 of administration or 22 µg/mL at day 28 of administration; and (c) a mean $C_{min}$ of 3.8 µg/mL at day 1 of administration or 3.4 µg/mL at day 28 of administration.

In one embodiment, the invention relates to a solid dosage form comprising 250 mg, 500 mg, 750 mg or 1000 mg of 3-[5-(2-fluoro-phenyl)-[1,2,4]oxadiazol-3-yl]-benzoic acid or a pharmaceutically acceptable salt, solvate or hydrate thereof which when administered to a patient in need thereof in three daily doses of 20 mg/kg, 20 mg/kg and 40 mg/kg, respectively, provides an in vivo plasma profile with a 90% CI for a natural-log transformed ratio within 80% to 125%, 90% to 115% or 95% to 110% for at least one of the following bioavailability parameters for 3-[5-(2-fluoro-phenyl)-[1,2,4]oxadiazol-3-yl]-benzoic acid or a pharmaceutically acceptable salt, solvate or hydrate thereof:

(a) a mean $AUC_{0-24}$ of 866 µg·hour/mL at day 1 of administration or 490 µg·hour/mL at day 28 of administration;

(b) a mean $C_{max}$ of 76 µg/mL at day 1 of administration or 46 µg/mL at day 28 of administration; and (c) a mean $C_{min}$ of 9.6 µg/mL at day 1 of administration or 6.7 µg/mL at day 28 of administration.

While it is recommended that the unit dosage formulations described herein are stored at between about 2° C. to about 8° C., the unit dosage formulations can be stored at room temperature for about 48 hours prior to reconstitution. In one embodiment, reconstitution of a 250 mg unit dosage formulation of 3-[5-(2-fluoro-phenyl)-[1,2,4]oxadiazol-3-yl]-benzoic acid or a pharmaceutically acceptable salt, solvate or hydrate thereof is carried out by the addition of about 10 mL of water directly in a bottle containing 3-[5-(2-fluoro-phenyl)-[1,2,4]oxadiazol-3-yl]-benzoic acid or a pharmaceutically acceptable salt, solvate or hydrate thereof to achieve a concentration of about 25 mg/mL in the total volume of suspension. For a 1000 mg unit dosage formulation of 3-[5-(2-fluoro-phenyl)-[1,2,4]oxadiazol-3-yl]-benzoic acid or a pharmaceutically acceptable salt, solvate or hydrate thereof, about 20 mL of water is added directly in the bottle containing 3-[5-(2-fluoro-phenyl)-[1,2,4]oxadiazol-3-yl]-benzoic acid or a pharmaceutically acceptable salt, solvate or hydrate thereof to achieve a concentration of about 50 mg/mL in the total volume of suspension. Immediately after water is added, the bottle is capped and shaken gently by hand for at least about 30 seconds to achieve a homogeneous suspension. Although the reconstituted suspension may remain in the original plastic bottle for up to 24 hours before ingestion, it is recommended that the drug be taken shortly after reconstitution. If there is a delay of more than about 15 minutes between reconstitution and dosing, it is recommended that the bottle should be reshaken gently by hand for at least about 30 seconds. It is recommended that the suspension be administered directly from the bottle. If the entire unit dosage form is to be administered, it is further recommended that the bottle be rinsed once with water and this rinse water be ingested to ensure that no powder is left in the bottle. If a partial amount of the unit dosage form is to be administered, a spoon or syringe can be used to obtain the appropriate dose.

Single unit dosage forms of the invention suitable for oral administration to a patient include, but are not limited to: sachets; cachets; tablets; caplets; capsules, such as soft elastic gelatin capsules; troches; lozenges; dispersions; powders; solutions; liquid dosage forms, including suspensions (e.g., aqueous or non-aqueous liquid suspensions); emulsions (e.g., oil-in-water emulsions, or a water-in-oil liquid emulsion); and elixirs. In one embodiment, the invention relates to a colloid solution or a solution with additional active agent, above the saturating concentration. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

This invention further encompasses anhydrous pharmaceutical compositions and dosage forms comprising 3-[5-(2-fluoro-phenyl)-[1,2,4]oxadiazol-3-yl]-benzoic acid or a pharmaceutically acceptable salt, solvate or hydrate thereof. Anhydrous pharmaceutical compositions and dosage forms of the invention can be prepared using anhydrous or low moisture containing ingredients and low moisture or low humidity conditions.

Typical oral dosage forms of the invention are prepared by combining the active ingredient(s) in an intimate admixture with at least one carrier or excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents (e.g., vanilla extract), preservatives, and coloring agents. Examples of excipients suitable for use in solid oral dosage forms (e.g., powders, tablets, sachets, capsules, and caplets) include, but are not limited to, starches, sugars, micro-crystalline cellulose, diluents, granulating agents, lubricants, binders, and disintegrating agents.

Particularly preferred unit dosage formulations are powder formulations comprising an effective amount of the active agent which are suitable for reconstitution in a pharmaceutically acceptable solvent (e.g., water, milk, a carbonated beverage, juice, apple sauce, baby food or baby formula) and subsequent oral administration. In a particular embodiment, the powder can optionally contain one or more carriers or excipients in combination with the active agent. In another embodiment, the powder can be stored in a sealed container prior to administration or reconstitution. In yet another embodiment, the powder can be encapsulated (e.g., in a gelatin capsule).

5. EXAMPLES

The following examples are offered by way of illustration and not limitation.

5.1 Example 1: Preparation of 3-[5-(2-Fluoro-phenyl)-[1,2,4]oxadiazol-3-yl]-benzoic Acid

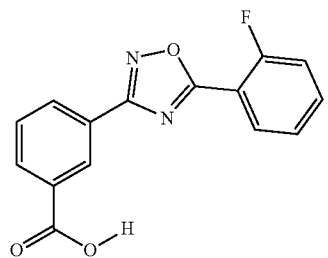 [SMILES: O=C(O)c1cccc(-c2noc(-c3ccccc3F)n2)c1]

Processes for the preparation of 3-[5-(2-fluorophenyl)-[1,2,4]oxadiazol-3-yl]-benzoic acid are described in U.S. Pat. No. 6,992,096 B2, issued Jan. 31, 2006, and U.S. patent application Ser. No. 11/899,813, filed Sep. 9, 2007, both of which are incorporated by reference in their entirety. A representative example of a process for the preparation of 3-[5-(2-fluorophenyl)-[1,2,4]oxadiazol-3-yl]-benzoic acid is set forth below.

To a solution of 3-Cyanobenzoic acid (44.14 g, 300 mmol) in DMF (0.6 L) was added $K_2CO_3$ (62.19 g, 450 mmol) and then stirred for 30 min at room temperature. To the suspension was added methyl iodide (28 mL, 450 mmol) over 20 min, and the reaction mixture was stirred further 4 h at room temperature. The reaction mixture was poured to 1.2 L of ice water and stirred for 30 min, and the precipitate was filtered off. The white cake was dissolved in methanol (70 mL), and then re-precipitated in cold water. The desired product was obtained as a white powder with 79% yield (38 g, 99% purity by LC/UV). $^1$H-NMR (CDCl$_3$) δ 8.85 (2H), 8.28 (1H), 8.02 (1H), 4.17 (3H).

To a solution of 3-Cyanobenzoic acid methyl ester (50 g, 310 mmol) in ethanol (500 mL) was added 50% aqueous hydroxylamine (41 mL, 620 mmol) at room temperature. The reaction mixture was stirred for 1 h at 100° C. and the solvents were removed under reduced pressure. The oily residue was dissolved in 20/80 ethanol/toluene (50 mL×2) and then concentrated again. The desired ester (61 g, quan. yield) was obtained as a white powder with 98% purity (LC/UV). $^1$H-NMR (CDCl$_3$) δ 9.76 (1H), 8.24 (1H), 7.82 (2H), 7.51 (1H), 5.92 (2H), 3.82 (3H).

To a solution of 3-(N-Hydroxycarbamimidoyl)-benzoic acid methyl ester (60 g, 310 mmol) in anhydrous THF (200 mL) was added diisopropylethylamine (75 mL, 434 mmol) at 5° C., and then to the mixture was added 2-fluorobenzoyl chloride (48.1 mL, 403 mmol) over 20 min. The reaction mixture was stirred for 1 h at room temperature. The precipitate was filtered off and the filtrate was concentrated under reduced pressure. The residue was dissolved in ethylacetate (400 mL) and then washed with water (200 mL×2). The solvent was removed under reduced pressure and the desired product was crystallized in 60% ethylacetate in hexane to yield the desired product (81 g, 83% yield) as a white solid. $^1$H-NMR (CDCl$_3$) δ 8.18 (1H), 8.03 (3H), 7.48 (2H), 7.18 (2H), 5.61 (2H), 3.82 (3H).

44 g of 3-(N-2-Fluorobenzoylcarbamimidoyl)-benzoic acid methyl ester in toluene (500 mL) was refluxed for 4 h at 130° C. using Dean-Stark apparatus. The reaction mixture was stirred at 5° C. for 18 h. The white precipitate was filtered off and the filtrate was concentrated, crystallized again in toluene. The desired oxadiazole (38 g, 92% yield) was obtained as a white solid with 99% purity (LC/UV). $^1$H-NMR (CDCl$_3$) δ 8.91 (1H), 8.38 (1H), 8.15 (2H), 7.62 (2H), 7.35 (2H), 3.95 (3H).

To a solution of 3-[5-(2-Fluoro-phenyl)-[1,2,4]oxadiazol-3-yl]-benzoic acid methyl ester (3.3 g, 11 mmol) in THF (40 mL) was added 1.5M aqueous NaOH (10 mL, 14 mmol). The reaction mixture was refluxed for 2 h at 100° C. The organic solvent was removed and the aqueous solution was diluted with water (50 mL), and then acidified with aqueous HCl. The white precipitate was filtered off and the white cake was washed with cold water and then dried using lyophilizer. The desired acid (3.0 g, 96% yield) was obtained as a white powder with 98% purity (LC/UV). Melting point 242° C.; IR 3000 (Aromatic C—H), 1710 (C═O); $^1$H-NMR (D$_6$-DMSO) δ 8.31 (1H), 8.18 (2H), 8.08 (1H), 7.88 (2H), 7.51 (2H); $^{13}$C-NMR (D$_6$-DMSO) δ □172.71, 167.38, 166.48, 161.25, 135.80, 132.24, 131.79, 131.79, 131.08, 130.91, 129.81, 127.76, 125.48, 117.38, 111.70; $^{19}$F-NMR (D$_6$-DMSO) δ □109.7.

Pharmaceutically acceptable salts of 3-[5-(2-Fluoro-phenyl)-[1,2,4]oxadiazol-3-yl]-benzoic acid can be prepared using methods known to those skilled in the art. The sodium salt can be prepared as follows. To a solution of 3-[5-(2-Fluoro-phenyl)-[1,2,4]oxadiazol-3-yl]-benzoic acid methyl ester (33 g, 111 mol) in THF (400 mL) was added 1.5M aqueous NaOH (100 mL, 144 mmol). The reaction mixture was refluxed for 2 h at 100° C. The organic solvent was removed under reduced pressure and the aqueous solution was stirred 2 h at 5° C. The white precipitate was filtered off and the filtrate was concentrated and precipitated again in water. The white cake was washed with cold water and then dried using lyophilizer. The desired salt (33 g, 96% yield) was obtained as a white powder with 98.6% purity (LC/UV).

5.2 Example 2: Oral Treatment of Nonsense-Mutation-Mediated Cystic Fibrosis

The present example sets forth an illustrative dosing regimen useful for the treatment of nonsense-mutation-mediated Cystic Fibrosis.

3-[5-(2-Fluoro-phenyl)-[1,2,4]oxadiazol-3-yl]-benzoic acid or a pharmaceutically acceptable salt, solvate or hydrate thereof is provided as a vanilla-flavored powder for suspension. The drug is manufactured under current Good Manufacturing Practice conditions (cGMP). The formulation can include binding and suspending agents, surfactants, and various minor excipients that aid in the manufacturing process. The mixture can be packaged in 40 mL plastic (high-density polyethylene [HDPE]) bottles sealed with a foil seal and a white plastic, childproof cap. Each bottle can contain 125, 250 or 1000 mg of the drug substance, which is 25.0% of the total formulation weight. Alternatively, the mixture can be provided in a sachet formulation, such as set forth in Example 6. Excipients (and their proportions of the total formulation weight) include a suspending agent (LITESSE® Ultra [refined polydextrose]—25.7%), a binding agent that can also provide taste-masking (mannitol—25.0%), surfactant agents (polyethylene glycol 3350—12.8% and LUTROL® micro F127 [poloxamer 407 powder]—3.7%), a disintegrant (crospovidone—5.0%), and other excipients, each less than 2% (hydroxyethyl cellulose, vanilla flavor, magnesium stearate [non-bovine], and colloidal silica) can be present. Bottle labels indicate the identity of the drug substance, the lot number, the amount of the drug substance, and the storage conditions (e.g., room temperature or refrigeration at 5° to 8° C.).

Dosing of the drug substance is based on milligrams of drug per kilogram of patient body weight. The dose of the drug substance can be rounded to be consistent with the available bottle sizes. The dosing scheme ensures that the total actual dose given is never <50 mg below or >250 mg above the intended dose (i.e., is always within 5 mg/kg of the assigned dose level). For example, a patient weighing 40 kg being treated with the 4 mg/kg dose would have a calculated dose of 160 mg. This patient would receive one 250 mg bottle (250 mg total) or 6.25 mg/kg/dose. The same patient when treated with the 8 mg/kg dose in the evening would have a calculated dose of 320 mg and would receive two 250 mg bottles (500 mg total) or 12.5 mg/kg. The same patient treated with the 10 mg/kg dose would have a calculated dose of 400 mg and would receive two 250 mg bottles (500 mg total) or 12.5 mg/kg. The same patient when treated with the 20 mg/kg dose in the evening would have a calculated dose of 800 mg and would receive one 1000 mg bottle (1000 mg total) or 25 mg/kg.

The reconstitution and dosing of the drug product is done at room temperature. No specific warming of the drug product is necessary before reconstitution. The drug product can be reconstituted with any pharmaceutically acceptable solvent (e.g., water, milk, a carbonated beverage, juice, apple sauce, baby food or baby formula). For each 250 mg bottle provided, ~10 mL of water or other pharmaceutically acceptable solvent is added to achieve a concentration of about 25 mg/mL in the total volume of suspension. For each 1000 mg bottle provided, ~20 mL of water or other pharmaceutically acceptable solvent is added to achieve a concentration of about 50 mg/mL in the total volume of suspension. Immediately after water or other pharmaceutically acceptable solvent is added to the dry study medication, the bottle(s) is capped and shaken vigorously by hand for about 60 seconds to achieve homogeneity of suspension. Although the suspension may remain in the original plastic bottle for up to 24 hours before ingestion, it is recommended that the drug be taken shortly after reconstitution. If there is a delay of more than 15 minutes between reconstitution and dosing, the bottle should be reshaken vigorously by hand for about 60 seconds.

Treatment is administered continuously for as long as necessary to a patient having or susceptible to having Cystic Fibrosis. Table 1 sets forth illustrative daily dosing regimens for 3-[5-(2-fluoro-phenyl)-[1,2,4]oxadiazol-3-yl]-benzoic acid or a pharmaceutically acceptable salt, solvate or hydrate thereof wherein administration occurs three times per day at 6-, 6-, and 12-hour intervals (e.g., ~7:00 AM, ~1:00 PM and ~7:00 PM) with food. In a particular embodiment, the patient is administered 3-[5-(2-fluoro-phenyl)-[1,2,4]oxadiazol-3-yl]-benzoic acid or a pharmaceutically acceptable salt, solvate or hydrate thereof as set forth in Table 1 continuously for 14 days, followed by 14 days without treatment, followed by an additional 14 days of administration, followed by an additional 14 days without treatment. In another particular embodiment, the patient is administered 3-[5-(2-fluoro-phenyl)-[1,2,4]oxadiazol-3-yl]-benzoic acid or a pharmaceutically acceptable salt, solvate or hydrate thereof as set forth in Table 1 continuously for 14 days at three daily doses of 4 mg/kg, 4 mg/kg and 8 mg/kg, followed by 14 days without treatment, followed by an additional 14 days of administration at three daily doses of 10 mg/kg, 10 mg/kg and 20 mg/kg, followed by an additional 14 days without treatment. In certain embodiments, a single daily dosing regimen set forth in Table 1 is followed each day. In other embodiments, different dosing regimens set forth in Table 1 can be followed on different days.

TABLE 1

| | Dosing Scheme | | | |
|---|---|---|---|---|
| | 1 | 2 | 3 | 4 |
| Regimen | TID dosing with food | TID dosing with food | TID dosing with food | TID dosing with food |
| Schedule | Continuous Daily Admin. | Continuous Daily Admin. | Continuous Daily Admin. | Continuous Daily Admin. |
| Time | | Dose | | |
| ~7:00 AM | 4 mg/kg | 7 mg/kg | 10 mg/kg | 20 mg/kg |
| ~1:00 PM | 4 mg/kg | 7 mg/kg | 10 mg/kg | 20 mg/kg |
| ~7:00 PM | 8 mg/kg | 14 mg/kg | 20 mg/kg | 40 mg/kg |

Abbreviations: TID = three times per day

Patients preferably take the drug within 30 minutes after a meal; ideally the drug will be taken at approximately 6-, 6, and 12-hour intervals (e.g., at ~7:00 AM after breakfast, ~1:00 PM after lunch, and at ~7:00 PM after supper). Patients ingest the drug by filling each bottle with the required amount of water or other pharmaceutically acceptable solvent, capping and shaking each bottle for about 60 seconds, and then ingesting the contents of the required number and size of bottles per dose. The entire dose of reconstituted drug is to be taken at one time. After ingestion, each dosing bottle is half-filled with water or another pharmaceutically acceptable solvent, capped and shaken, and this water or other pharmaceutically acceptable solvent from the bottle is ingested by the patient. This rinse procedure is carried out once. In certain embodiments, the drug is provided as a sachet. In these embodiments, the appropriate amount of the drug can be weighed or measured and combined with an appropriate pharmaceutically acceptable solvent prior to administration.

5.3 Example 3: Oral Treatment of Nonsense-Mutation-Mediated Duchenne Muscular Dystrophy The present example sets forth an illustrative dosing regimen useful for the treatment of nonsense-mutation-mediated Duchenne Muscular Dystrophy.

3-[5-(2-Fluoro-phenyl)-[1,2,4]oxadiazol-3-yl]-benzoic acid or a pharmaceutically acceptable salt, solvate or hydrate thereof is provided as a vanilla-flavored powder for suspension. The drug is manufactured under current Good Manufacturing Practice conditions (cGMP). The formulation can include binding and suspending agents, surfactants, and various minor excipients that aid in the manufacturing process. The mixture can be packaged in 40 mL plastic (high-density polyethylene [HDPE]) bottles sealed with a foil seal and a white plastic, childproof cap. Each bottle can contain 125, 250 or 1000 mg of the drug substance, which is 25.0% of the total formulation weight. Alternatively, the mixture can be provided in a sachet formulation, such as set forth in Example 6. Excipients (and their proportions of the total formulation weight) include a suspending agent (LITESSE® Ultra [refined polydextrose]~25.7%), a binding agent that can also provide taste-masking (mannitol—25.0%), surfactant agents (polyethylene glycol 3350—12.8% and LUTROL® micro F127 [poloxamer 407 powder]—3.7%), a disintegrant (crospovidone—5.0%), and other excipients, each less than 2% (hydroxyethyl cellulose, vanilla flavor, magnesium stearate [non-bovine], and colloidal silica) can be present. Bottle labels indicate the identity of the drug substance, the lot number, the amount of the drug substance, and the storage conditions (e.g., room temperature or refrigeration at 5° to 8° C.).

Dosing of the drug is based on milligrams of drug per kilogram of patient body weight. The total volume corresponding to the total milligram amount of drug to be administered to a patient should be calculated. For example, if a 30-kg patient is to get 4 mg/kg, then the dose to be delivered will be 30×4=120 mg. This patient should be dosed using the 250 mg dose bottle. Since each mL of the suspension in the 250 mg dose bottle contains 250/10=25 mg of the drug, this patient should get 120/25=~5 mL of the suspension for each 4 mg/kg dose). The same patient when treated with the 8 mg/kg dose in the evening would have a calculated dose of 240 mg and would receive one 250 mg bottle (10 mL suspension). These volumes of the suspensions for the respective doses should be withdrawn from the drug bottle using a plastic oral dosing syringe. For transfer of fractional volumes of <10 (for 250 mg bottle) or <20 mL (for 1000 mg bottle), the desired amount should be withdrawn from the study medication bottle into a dosing syringe of an appropriate type and size (e.g., a Baxa, Exacta-Med, calibrated, latex-free, plastic, oral dosing syringe) and dosed using the same syringe. During the same 24 hours after reconstitution, >1 dose may be taken from the same bottle of suspension; however, reconstituted drug should not be stored beyond 24 hours with the intention of using this material again for multiple doses in the same patient. If the total amount of drug to be taken in 1 day exceeds 10 mL (for 250 mg bottle) or 20 mL (for 1000 mg bottle) of the reconstituted drug, then a new bottle of drug should be used for each dosing.

The reconstitution and dosing of the drug product is done at room temperature. No specific warming of the drug product is necessary before reconstitution. The drug can be reconstituted with any pharmaceutically acceptable solvent (e.g., water, milk, a carbonated beverage, juice, apple sauce, baby food or baby formula). For each 250 mg bottle provided, ~10 mL of water or other pharmaceutically acceptable solvent is added to achieve a concentration of about 25 mg/mL in the total volume of suspension. For each 1000 mg bottle provided, ~20 mL of water or other pharmaceutically acceptable solvent is added to achieve a concentration of about 50 mg/mL in the total volume of suspension. Immediately after water or other pharmaceutically acceptable solvent is added to the dry study medication, the bottle(s) is capped and shaken vigorously by hand for about 60 seconds to achieve homogeneity of suspension. Although the suspension may remain in the original plastic bottle for up to 24 hours before ingestion, it is recommended that the drug be taken shortly after reconstitution. If there is a delay of more than 15 minutes between reconstitution and dosing, the bottle should be reshaken vigorously by hand for about 60 seconds.

Treatment is administered continuously for as long as necessary to a patient having or susceptible to having Duchenne Muscular Dystrophy. Table 2 sets forth illustrative daily dosing regimens for 3-[5-(2-fluoro-phenyl)-[1,2,4]oxadiazol-3-yl]-benzoic acid or a pharmaceutically acceptable salt, solvate or hydrate thereof wherein administration occurs three times per day at 6-, 6-, and 12-hour intervals (e.g., ~7:00 AM, ~1:00 PM and ~7:00 PM) with food. In a particular embodiment, the patient is administered 3-[5-(2-fluoro-phenyl)-[1,2,4]oxadiazol-3-yl]-benzoic acid or a pharmaceutically acceptable salt, solvate or hydrate thereof in one of the dosing regimens set forth in Table 2 continuously for 28 days. In certain embodiments, a single daily dosing regimen set forth in Table 2 is followed each day. In other embodiments, different dosing regimens set forth in Table 2 can be followed on different days. In certain embodiments, the drug is provided as a sachet. In these embodiments, the appropriate amount of the drug can be weighed or measured and combined with an appropriate pharmaceutically acceptable solvent prior to administration.

TABLE 2

| | Dosing Scheme | | | |
|---|---|---|---|---|
| | 1 | 2 | 3 | 4 |
| Regimen | TID dosing with food | TID dosing with food | TID dosing with food | TID dosing with food |
| Schedule | Continuous Daily Admin. | Continuous Daily Admin. | Continuous Daily Admin. | Continuous Daily Admin. |
| Time | | Dose | | |
| ~7:00 AM | 4 mg/kg | 7 mg/kg | 10 mg/kg | 20 mg/kg |
| ~1:00 PM | 4 mg/kg | 7 mg/kg | 10 mg/kg | 20 mg/kg |
| ~7:00 PM | 8 mg/kg | 14 mg/kg | 20 mg/kg | 40 mg/kg |

Abbreviations: TID = three times per day

Patients are administered the drug within 30 minutes after a meal; ideally the drug will be taken at approximately 6-, 6, and 12-hour intervals (e.g., at ~7:00 AM after breakfast, ~1:00 PM after lunch, and at ~7:00 PM after supper). Patients ingest the drug by filling each bottle with the required amount of water or other pharmaceutically acceptable solvent, capping and shaking each bottle for about 60 seconds, withdrawing the appropriate amount of volume from the bottle using an oral dosing syringe and ingesting the contents directly from the dosing syringe. The entire calculated volume of reconstituted drug corresponding to the dose is to be taken at one time. After ingestion of the drug, the dosing syringe should be filled with the same volume of water or other pharmaceutically acceptable solvent as the dose volume, and should be ingested by the patient. This rinse procedure should be carried out once.

Efficacy of treatment can be determined by measuring the change from a baseline measurement of dystrophin levels in a biopsy of the foot muscle extensor digitorum brevis (EDB).

5.4 Example 4: Preparation of Unflavored Dosages of 3-[5-(2-Fluoro-phenyl)-[1,2,4]oxadiazol-3-yl]-benzoic Acid or a Pharmaceutically Acceptable Salt, Solvate or Hydrate Thereof 3-[5-(2-Fluoro-phenyl)-[1,2,4]oxadiazol-3-yl]-benzoic acid or a pharmaceutically acceptable salt, solvate or hydrate thereof is provided as a powder for suspension. The drug is manufactured under current Good Manufacturing Practice conditions (cGMP). The drug can be intimately mixed with binding and suspending agents, surfactants, and various minor excipients that aid in the manufacturing process. The mixture is packaged in a 40 mL plastic (high-density polyethylene [HDPE]) bottle sealed with a foil seal and a white plastic, childproof cap. Each bottle can contain about 35 mg, about 70 mg, about 125 mg, about 140 mg, about 175 mg, about 250 mg, about 280 mg, about 350 mg, about 560 mg, about 700 mg, about 1000 mg or about 1400 mg of 3-[5-(2-fluoro-phenyl)-[1,2,4]oxadiazol-3-yl]-benzoic acid or a pharmaceutically acceptable salt, solvate or hydrate thereof. Excipients (and their proportions of the total formulation weight) optionally include a suspending agent (LITESSE® Ultra [refined polydextrose]—25.7%), a binding agent that can also provide taste-masking (mannitol—25.0%), surfactant agents (polyethylene glycol 3350—12.8% and LUTROL® micro F127 [poloxamer 407 powder]—3.7%), a disintegrant (crospovidone—5.0%), and other excipients, each less than 2% (cab-o-sil, hydroxyethyl cellulose, magnesium stearate [non-bovine], and colloidal silica) can be present. The bottle is then labeled to indicate the identity of the drug substance, the lot number, the amount of the drug substance, and the storage conditions (e.g., refrigeration at 5° to 8° C.). Prior to administration, the drug product is reconstituted in an appropriate volume of a pharmaceutically acceptable solvent (e.g., water, milk, a carbonated beverage, juice, apple sauce, baby food or baby formula).

5.5 Example 5: Preparation of Flavored Dosages of 3-[5-(2-Fluoro-phenyl)-[1,2,4]oxadiazol-3-yl]-benzoic Acid or a Pharmaceutically Acceptable Salt, Solvate or Hydrate Thereof 3-[5-(2-Fluoro-phenyl)-[1,2,4]oxadiazol-3-yl]-benzoic acid or a pharmaceutically acceptable salt, solvate or hydrate thereof is provided as a vanilla-flavored (e.g., by addition of vanilla extract) powder for suspension. The drug is manufactured under current Good Manufacturing Practice conditions (cGMP). The drug can be intimately mixed with binding and suspending agents, surfactants, and various minor excipients that aid in the manufacturing process. The mixture is packaged in a 40 mL plastic (high-density polyethylene [HDPE]) bottle sealed with a foil seal and a white plastic, childproof cap. Each bottle can contain about 35 mg, about 70 mg, about 125 mg, about 140 mg, about 175 mg, about 250 mg, about 280 mg, about 350 mg, about 560 mg, about 700 mg, about 1000 mg or about 1400 mg of 3-[5-(2-fluoro-phenyl)-[1,2,4]oxadiazol-3-yl]-benzoic acid or a pharmaceutically acceptable salt, solvate or hydrate thereof. Excipients (and their proportions of the total formulation weight) optionally include a suspending agent (LITESSE® Ultra [refined polydextrose]—25.7%), a binding agent that can also provide taste-masking (mannitol—25.0%), surfactant agents (polyethylene glycol 3350—12.8% and LUTROL® micro F127 [poloxamer 407 powder]—3.7%), a disintegrant (crospovidone—5.0%), and other excipients, each less than 2% (cab-o-sil, hydroxyethyl cellulose, vanilla flavor, magnesium stearate [non-bovine], and colloidal silica) can be present. The bottle is then labeled to indicate the identity of the drug substance, the lot number, the amount of the drug substance, and the storage conditions (e.g., refrigeration at 2° to 8° C.). Prior to administration, the drug product is reconstituted in an appropriate volume of a pharmaceutically acceptable solvent (e.g., water, milk, a carbonated beverage, juice, apple sauce, baby food or baby formula). The drug product can be stored at room temperature for up to 48 hours prior to reconstitution.

A number of references have been cited, the entire disclosure of which are incorporated herein by reference in their entirety.

5.6 Example 6: Sachet Formulation of 3-[5-(2-Fluoro-phenyl)-[1,2,4]oxadiazol-3-yl]-benzoic Acid or a Pharmaceutically Acceptable Salt, Solvate or Hydrate Thereof The mixture is packaged using a pouch or sachet that is comprised of multiple laminated layers that may include a paper layer, an aluminum foil layer and a surlyn layer. Each sachet can contain about 125 mg, about 250 mg, about 500 mg or about 1000 mg of 3-[5-(2-fluoro-phenyl)-[1,2,4] oxadiazol-3-yl]-benzoic acid or a pharmaceutically acceptable salt, solvate or hydrate thereof. Excipients (and their proportions of the total formulation weight) optionally include either of the following as set forth in Table 3 and Table 4.

TABLE 3

Formulation

| Ingredient | Weight % |
| --- | --- |
| 3-[5-(2-fluoro-phenyl)-[1,2,4]oxadiazol-3-yl]-benzoic acid or a pharmaceutically acceptable salt, solvate or hydrate thereof | 25.0 |
| Litesse ® Ultra | 24.75 |
| Polyethylene Glycol | 12.8 |
| Lutrol ® Micro | 3.7 |
| Mannitol | 25.0 |
| Hydroxyethyl Cellulose | 1.5 |
| Vanilla Flavor | 0.75 |
| Crospovidone | 5.0 |
| Cab-o-sil | 0.5 |
| Magnesium Stearate | 0.5 |
| Talc | 0.5 |

TABLE 4

Formulation

| Ingredient | Weight % |
| --- | --- |
| 3-[5-(2-fluoro-phenyl)-[1,2,4]oxadiazol-3-yl]-benzoic acid or a pharmaceutically acceptable salt, solvate or hydrate thereof | 25.0 |
| Litesse ® Ultra | 25.65 |
| Polyethylene Glycol | 12.8 |
| Lutrol ® Micro | 3.7 |
| Mannitol | 25.0 |
| Hydroxyethyl Cellulose | 1.5 |
| Vanilla Flavor | 0.75 |
| Crospovidone | 5.0 |
| Cab-o-sil | 0.1 |
| Magnesium Stearate | 0.5 |

The sachet is then labeled to indicate the identity of the drug substance, the lot number, the amount of the drug substance, and the storage conditions (e.g., refrigeration at 2° to 8° C.). Prior to administration, an appropriate amount of the drug product is reconstituted in an appropriate volume of a pharmaceutically acceptable solvent (e.g., water, milk, a carbonated beverage, juice, apple sauce, baby food or baby formula). The drug product can be stored at room temperature for up to 48 hours prior to reconstitution.

5.7 Example 7: Transepithelial Potential Difference (TEPD) Assay

The measurement of transepithelial potential difference (TEPD), also known as nasal potential difference, provides a sensitive evaluation of sodium and chloride transport directly in secretory epithelial cells via assessment of transepithelial bioelectric properties (Knowles et al., 1981, *N. Engl. J. Med.* 305(25):1489-95; Knowles et al., 1995, *Hum. Gene Ther.* 6:445). TEPD is performed in each nostril using standardized techniques (Standaert et al., 2004, *Ped. Pulm.* 37:385-92). In the procedure, a small plastic catheter is used to assess electrical differences across the outer cell membrane of nasal mucosa cells in the nostril. TEPD values are expressed in millivolts, or mV. A chloride conductance equal to or more electrically negative than −5.0 mV is generally considered to be in the normal range. TEPD assessments are made on the nasal epithelium cells lining the inferior turbinate because these cells are easier to access than the respiratory epithelial cells lining the lower airways, and have been shown to have the same ion transport characteristics (Knowles et al., 1981, *Am. Rev. Respir. Dis.* 124(4):484-90). TEPD assessments can also be made on rectal epithelial cells and lower respiratory epithelial cells. Because of the role of the CFTR protein in transporting chloride ions across cell membranes, and because of the absence of this protein, cystic fibrosis patients have an abnormal TEPD chloride conductance. As an endpoint, TEPD has the advantage that it can detect chloride transport changes that are a quantitative integration of the presence, functional activity, and apical location of the CFTR in airway cells. Furthermore, it is a direct measure of CFTR activity that is not likely to be affected by supportive or palliative treatments for CF (with the possible exception of systemically administered aminoglycoside antibiotics). Of importance is evidence that TEPD values can correlate with the degree of pulmonary dysfunction and radiographic abnormality (Ho et al., 1997, *Eur. Respir. J.* 10(9):2018-22; Fajac et al., 1998, *Eur. Respir. J.* 12(6):1295-300; Sermet-Gaudelus et al., 2005, *Am. J. Respit. Crit. Care Med.* 171(9):1026-1031). In particular, TEPD assessment of isoproterenol-induced CFTR chloride activity has demonstrated better predictive value than genotype in determining FEV1 and radiological score (Ho et al., 1997, *Eur Respir* 110(9):2018-22). Under baseline conditions, TEPD-assessed chloride channel activity is very unlikely to normalize spontaneously in patients with CF; any observed improvements in TEPD-assessed chloride channel activity are expected to specifically denote pharmacological activity of CFTR-correcting therapies. Accordingly, it has become the primary endpoint in Phase 1-2 pharmacological and gene replacement studies aimed at correcting CFTR dysfunction (Peckham et al., 1995, *AJ. Clin* Sci (London). 89(3):277-84; Wilschanski et al., 2003, *N. Engl. J. Med.* 349(15):1433-41).

5.8 Example 8: CFTR Immunofluorescence

The collection and processing of the nasal mucosal curettage from each nostril of a patient for measurement of CFTR protein by immunofluorescence and by quantification of CFTR mRNA is performed using standardized techniques (Clancy et al., 2001, *Am. J. Respir. Crit. Care Med.* 163(7): 1683-92; Amaral et al., 2004, *J. Cyst. Fibros.* 3 Suppl 2:17-23). The immunofluorescence staining of normal epithelial cells (for example, from nasal mucosal scrapings) reveals the presence of most of the CFTR protein at the apical surface. In animal models of nonsense-mutation-mediated CF or in patients with nonsense-mutation-mediated CF, CFTR staining is absent (e.g., in patients homozygous for a premature stop mutation) or is primarily observed in the perinuclear region (e.g., in patients with a ΔF508 mutation that prevents normal CFTR intracellular trafficking). Successful production of functional wild or non-wild type CFTR protein in both animal models and patients has been associated with reappearance of apical epithelial CFTR protein as assessed by immunofluorescence (Clancy et al., 2001, *Am. J. Respir. Crit. Care Med.* 163(7):1683-92; Wilschanski et al., 2003, *N. Engl. J. Med.* 349(15):1433-41).

5.9 Example 9: Pulmonary Function Tests

Pulmonary function tests, including $FEV_1$, FVC, and $MEF_{25-75}$, are measured using standard spirometry procedures. Assessments of pulmonary function (including $MEF_{25-75}$, FVC, and, particularly, $FEV_1$) have been acknowledged as definitive clinical endpoints in patients with CF (Food and Drug Administration, 62nd Anti-Infective Drugs Advisory Committee. Discussion of NDA for tobramycin solution for inhalation (TOBI®) for the management of cystic fibrosis patients. November, 1997; Tiddens, 2002, *Pediatr. Pulmonol.* 34(3): 228-31). $FEV_1$ and other pulmonary function testing measures have been shown to correlate with disease severity, predict morbidity in terms of health care utilization and IV antibiotic usage, and indicate the risk of CF-related mortality (Food and Drug Administration, 62nd Anti-Infective Drugs Advisory Committee. Discussion of NDA for tobramycin solution for inhalation (TOBI®) for the management of cystic fibrosis patients. November, 1997). Pulmonary function testing is simple to administer (even in patients as young as 7 years of age), and uses standardized equipment and techniques that are widely available. Interpretation is performed using well-established normative equations that account for patient age, height, and gender. Improvement in $FEV_1$ has been acknowledged as quantitatively demonstrating meaningful clinical benefit in CF, and has served as the basis for regulatory approval of dornase alfa and inhaled tobramycin (Food and Drug Administration, 62nd Anti-Infective Drugs Advisory Committee. Discussion of NDA for tobramycin solution for inhalation (TOBI®) for the management of cystic fibrosis patients. November, 1997).

5.10 Example 10: Phase 2 Study of 3-[5-(2-fluoro-phenyl)-[1,2,4]oxadiazol-3-yl]-benzoic as an Oral Treatment for Nonsense-Mutation-Mediated Cystic Fibrosis Patients must have met all of the following conditions to be eligible for enrollment into the study:

1. Diagnosis of CF based on documented evidence of a conclusively abnormal sweat test (sweat chloride >60 mEq/liter by pilocarpine iontophoresis (LeGrys, Sweat testing: Sample collection and quantitative analysis: Approved guidelines—Second edition. National Committee for Clinical Laboratory Standards 2000; Vol 20:14));

2. Abnormal chloride secretion as measured by TEPD (a more positive than −5 mV TEPD assessment of chloride secretion with chloride-free amiloride and isoproterenol);

3. Presence of a nonsense mutation in one of the alleles of the cftr gene;

4. Documentation that cftr gene sequencing has been performed;

5. Age ≥18 years;

6. Body weight ≥40 kg;

7. $FEV_1$≥40% of predicted for age, gender, and height (Knudson standards) (Knudson, 1983, *Am. Rev. Respir. Dis.* 127: 725-734);

8. Oxygen saturation (as measured by pulse oximetry) ≥92% on room air;

9. Willingness of male and female patients, if not surgically sterile, to abstain from sexual intercourse or employ a barrier or medical method of contraception during the study drug administration and follow-up periods;

10. Negative pregnancy test (for females of childbearing potential);

11. Willingness and ability to comply with scheduled visits, drug administration plan, study procedures (including TEPD measurements, clinical laboratory tests, and PK sampling), and study restrictions;

12. Ability to provide written informed consent; and

13. Evidence of personally signed and dated informed consent document indicating that the patient has been informed of all pertinent aspects of the trial.

The presence of any of the following conditions excluded a patient from enrollment in the study:

1. Prior or ongoing medical condition (e.g., concomitant illness, psychiatric condition, alcoholism, drug abuse), medical history, physical findings, ECG findings, or laboratory abnormality that, in the investigator's opinion, could adversely affect the safety of the patient, makes it unlikely that the course of treatment or follow-up would be completed, or could impair the assessment of study results;

2. Ongoing acute illness including acute upper or lower respiratory infections within 2 weeks before start of study treatment;

3. History of major complications of lung disease (including recent massive hemoptysis or pneumothorax) within 2 months prior to start of study treatment;

4. Abnormalities on screening chest x-ray suggesting clinically significant active pulmonary disease other than CF, or new, significant abnormalities such as atelectasis or pleural effusion which may be indicative of clinically significant active pulmonary involvement secondary to CF;

5. Positive hepatitis B surface antigen, hepatitis C antibody test, or human immunodeficiency virus (HIV) test;

6. Hemoglobin <10 g/dL;

7. Serum albumin <2.5 g/dL;

8. Abnormal liver function (serum total bilirubin > the upper limit of normal, or serum ALT, AST, or GGT>2.0 times the upper limit of normal);

9. Abnormal renal function (serum creatinine >1.5 times upper limit of normal);

10. Pregnancy or breast-feeding;

11. History of solid organ or hematological transplantation;

12. Exposure to another investigational drug within 14 days prior to start of study treatment;

13. Ongoing participation in any other therapeutic clinical trial;

14. Ongoing use of thiazolidinedione peroxisome proliferator-activated receptor gamma (PPAR γ) agonists, e.g., rosiglitazone (AVANDIA® or equivalent) or pioglitazone (ACTOS® or equivalent);

15. Change in intranasal medications (including use of corticosteroids, cromolyn, ipratropium bromide, phenylephrine, or oxymetazoline) within 14 days prior to start of study treatment;

16. Change in treatment with systemic or inhaled corticosteroids within 14 days prior to start of study treatment;

17. Use of or requirement for inhaled gentamicin or amikacin within 14 days prior to start of study treatment or during study treatment; or 18. Requirement for systemic aminoglycoside antibiotics within 14 days prior to start of study treatment.

3-[5-(2-Fluoro-phenyl)-[1,2,4]oxadiazol-3-yl]-benzoic acid was provided in a formulation described herein. 15 patients (12 from a Phase 2 trial being conducted in Israel and 3 from a Phase 2 trial being conducted in the United States; seven patients were male and 8 were female; patients had a median age of 22 years; and all patients had multiple signs and symptoms of cystic fibrosis, including some degree of lung dysfunction) were orally administered 3-[5-(2-fluoro-phenyl)-[1,2,4]oxadiazol-3-yl]-benzoic acid according to the following 56 day schedule: administration of 3-[5-(2-fluoro-phenyl)-[1,2,4]oxadiazol-3-yl]-benzoic acid three times per day (TID) at 4 mg/kg, 4 mg/kg and 8 mg/kg for 14 days, followed by no treatment for 14 days (Cycle 1, consisting of 28 days), followed by administration of 3-[5-(2-fluoro-phenyl)-[1,2,4]oxadiazol-3-yl]-benzoic acid three times per day (TID) at 10 mg/kg, 10 mg/kg and 20 mg/kg for 14 days, followed by no treatment for 14 days (Cycle 2, consisting of 28 days).

Clinical endpoints were evaluated using the procedures set forth above. TEPD measurements were made prior to treatment and on days 14 and 28 of Cycle 1 and Cycle 2. Nasal mucosal curettage was collected from each nostril of each patient prior to treatment and on days 14 and 28 of Cycle 1 and Cycle 2. Pulmonary tests, including $FEV_1$, FVC and $MEF_{25-75}$, were measured prior to treatment, on day −1 of Cycle 2, on day 13 or 14 of Cycle 1 and day 13 or 14 of Cycle 2 in the study being conducted in Israel and the same parameters were measured prior to treatment and on day 13 or 14 of Cycle 2 in the study being conducted in the United States.

Mean Change in TEPD Chloride Conductance.

This is the average of the changes from the beginning to the end of the treatment period in TEPD chloride conductance within each study participant. For example, if the changes in TEPD chloride conductance within each of three participants were −7.0 mV, −2.0 mV and −9.0 mV, the mean change in TEPD chloride conductance among these participants would be −6.0 mV.

Percentage of Patients with a Chloride Conductance Response.

This is the percentage of patients who demonstrated a TEPD chloride conductance response at the end of treatment with 3-[5-(2-fluoro-phenyl)-[1,2,4]oxadiazol-3-yl]-benzoic acid. For purposes of the trials, a chloride conductance response is defined as a TEPD chloride conductance improvement of at least −5 mV. For example, in a patient with a TEPD chloride conductance value of +1.0 mV at baseline and a TEPD chloride conductance value of −6.0 mV at the end of treatment, the TEPD chloride conductance improvement would be −7.0 mV, representing a chloride conductance response.

Percentage of Patients with Improvements of TEPD Chloride Conductance Values into the Normal Range.

As noted above, a chloride conductance equal to or more electrically negative than −5.0 mV is generally considered to be in the normal range. As such, a patient with a TEPD chloride conductance value of +1.0 mV at baseline would be considered to have an abnormal value because the value is more electrically positive than −5.0 mV. If, at the end of treatment, that patient's TEPD chloride conductance value improved to −6.0 mV, this would represent an improvement into the normal range because the improved value is more electrically negative than −5.0 mV.

Based on patient gender, age and height, the mean $FEV_1$ value at study entry was 66% of normal and the mean FVC value at study entry was 80% of normal. Fourteen of the 15 patients included in the analysis had airway colonization with *Pseudomonas aeruginosa*, a common bacterial infection in cystic fibrosis patients that can lead to serious pneumonia. Fourteen of the 15 patients also had pancreatic insufficiency and required chronic pancreatic enzyme replacement therapy. Patients had low body weights, with a mean weight of 58.3 kg at study entry.

Table 5 presents the TEPD results for the 5 patients. For each measurement, the results are presented on a best-of-nostrils and mean-of-both-nostrils basis. Historically, results of TEPD tests have typically been presented on a best-of-nostrils basis. However, recent guidelines established by the Cystic Fibrosis Therapeutics Development Network recommend that TEPD results be presented on both bases. Improvements in TEPD chloride conductance in patients with different types of nonsense mutations within the CFTR gene were noted.

TABLE 5

| TEPD Result | Lower Dose Level | | Higher Dose Level | |
|---|---|---|---|---|
| | Result | p-Value | Result | p-Value |
| Mean change in TEPD chloride conductance: | | | | |
| Best of nostrils | −9.0 mV | <0.001 | −6.4 mV | 0.010 |
| Mean of both nostrils | −6.7 mV | <0.001 | −4.4 mV | 0.023 |
| Number of patients with ≥ −5 mV improvement in TEPD chloride conductance: | | | | |
| Best of nostrils | 9/15 (60%) | <0.001 | 8/15 (53%) | <0.001 |
| Mean of both nostrils | 6/15 (40%) | 0.005 | 7/15 (47%) | <0.001 |
| Number of patients with improvement in TEPD chloride conductance to normal: | | | | |
| Best of nostrils | 8/15 (53%) | 0.008 | 8/15 (53%) | 0.008 |
| Mean of both nostrils | 6/15 (40%) | 0.032 | 7/15 (47%) | 0.016 |

The treatment effects at the lower and the higher 3-[5-(2-fluoro-phenyl)-[1,2,4]oxadiazol-3-yl]-benzoic acid dose levels were not statistically significant, suggesting that further dose escalation may not be necessary and that even lower doses of 3-[5-(2-fluoro-phenyl)-[1,2,4]oxadiazol-3-yl]-benzoic acid may be effective in improving TEPD chloride conductance. Statistically significant results and positive trends for secondary endpoints were also observed. In particular, although the trials were not been powered to detect statistical significant changes in secondary endpoints, statistically significant improvements from study entry to the end of the higher-dose treatment cycle in the patients' mean $FEV_1$, FVC and weight were observed. Table 6 presents the results. For the changes in lung function, one patient was not included because that patient did not have lung function measured at the end of the higher-dose treatment cycle.

TABLE 6

| Endpoint | Study Entry | End of Higher Dose Treatment | Change | p-Value |
|---|---|---|---|---|
| Lung function (expressed as a percentage of normal for gender, age and height): | | | | |
| Mean $FEV_1$ | 65.8% | 69.1% | 3.3% | 0.015 |
| Mean FVC | 80.2% | 85.1% | 4.9% | 0.037 |
| Weight | 58.3 kg | 59.0 kg | 0.7 kg | 0.012 |

In addition, although changes in patient's symptoms were not formally measured through the use of a quality-of-life questionnaire, trial investigators were requested to ask about changes in patients' cystic fibrosis symptoms. In the 15 patients included in the interim analysis, 6 reported general improvements in well being, 6 reported decrease in cough and 10 reported decreased mucus thickness and easier clearing of mucus.

5.11 Example 11: Dystrophin, Sarcoglycan, and Dystroglycan Expression by Immunofluorescence and Western Blotting Biopsy of the EDB muscle and overlying skin from one foot is performed under local anesthesia and conscious sedation (in some cases, general anesthesia may be required) prior to treatment, and from the other foot on the last day of treatment. The biopsy procedure is performed using standardized techniques (Stedman, 2000, Human Gene Therapy 11:777-90). The entire muscle belly (whenever possible) is removed in the procedure. At the time of collection of the biopsy prior to treatment, the muscle specimen is divided into at least 3 fragments and the biopsy specimen collected on the last day of treatment is divided into at least 2 fragments. The biopsy specimen is placed on a telfa gauze sponge moistened with Ringer's saline. The biopsy specimen is viewed at low power under a stereo dissection microscope to establish fiber orientation. The muscle is then transected using a sharp scalpel in a cross sectional fashion (perpendicular to the orientation of the fibers) whenever possible and allowed to rest for 2 minutes to allow for the cessation of spasm. The sample is then frozen in liquid nitrogen cooled isopentane, transferred to a liquid nitrogen reservoir and held 1 inch above the liquid/vapor interface for 2 minutes of slow cooling and isopentane evaporation before immersion in the liquid nitrogen, and wrapped into pre-cooled (in liquid nitrogen and stored on dry ice) foil labeled with the study number, site number, patient number, date, patient initials, and foot side (right foot or left foot).

All sample containers are clearly labeled in a fashion that identifies the subject and the collection date. Labels are fixed to the sample containers in a manner that prevents the label from becoming detached. Samples are shipped for analysis/culture/central review immediately after the procedure is performed. For detection of dystrophin, 3 commercially available antibodies that recognize the C-terminus, the N-terminus, and the rod domain of the protein are employed. For detection of the sarcoglycan and dystroglycan complex, commercially available antibodies against $\alpha$-, $\beta$-, $\gamma$-, and $\delta$-sarcoglycan, and $\beta$-dystroglycan are used when possible. Epifluorescence microscopy is used in the analysis; images are captured by CCD camera, after normalization of the fluorescence intensity against a normal muscle specimen. Images are stored digitally and preserved for future review, and final evaluation at the completion of the study. Tissues are also processed for detection of dystrophin, the sarcoglycans, and $\beta$-dystroglycan by Western blotting using the same antibodies. Microscopic images are captured and preserved for future review, and for final evaluation at the completion of the study. Remaining muscle tissue samples are preserved for confirmatory assays of mRNA and proteins involved in DMD. Immunostaining and Western blotting are employed for protein detection.

Muscle biopsies are commonly performed on DMD subjects as a component of diagnosis and as measures of therapeutic effect in the context of research studies. EDB has been chosen because it is not an essential muscle for daily activities and therefore sampling this muscle does not have adverse functional consequence for the subject. Because it is little used, the EDB muscle is unlikely to demonstrate substantial fibrotic replacement of muscle and thus provides an appropriate tissue for detection of dystrophin production. Sampling of the EDB muscle offers additional practical advantages because it is easy to identify, can be dissected under local anesthesia, and provides sufficient amounts of tissue to carry out the required analyses. Immunofluorescence and Western blotting are routine tests performed on muscle biopsy specimens to confirm the presence or absence of full-length dystrophin. An absence of dystrophin is viewed as confirmation of the diagnosis of DMD. Restoration of dystrophin, with localization to the muscle membrane, has been considered a direct measure of preclinical and clinical pharmacodynamic activity (Barton-Davis, 1999, *J. Clin. Invest.* 104(4):375-81; Politano, 2003, *Acta Myol.* 22(1):15-21).

5.12 Example 12: Upper and Lower Extremity Myometry

Upper and lower extremity myometry are performed using a hand-held myometer following standardized procedures (Beenakker, 2001, *Neuromuscul. Disord.* 11(5):441-6; Hyde, 2001, *Neuromuscul. Disord.* 11(2):165-70). It is recommended (depending on the subject's baseline functional status) that evaluated muscle groups include hip abductors, knee extensors, elbow flexors and extensors, and hand grip. Bilateral assessments can be done, and three measurements can be recorded from each muscle group on each side. These parameters are monitored prior to treatment, on the second to last day of treatment, and during a follow-up period after treatment. During the pre-treatment and treatment periods, the myometry procedures are performed prior to the muscle biopsy.

Myometry assessments using a hand-held dynamometer are a sensitive and reproducible measure of muscle strength in ambulatory and non-ambulatory subjects (Beenakker, 2001, *Neuromuscul. Disord.* 11(5):441-6; Hyde, 2001, *Neuromuscul. Disord.* 11(2):165-70). Inter-rater reliability in subjects with muscular dystrophy is high (Stuberg, 1988, *Phys. Ther.* 1988 68(6):977-82; Hyde, 2001, *Neuromuscul. Disord.* 11(2):165-70). As compared to manual muscle strength testing, myometry is a more sensitive and less complex measure of muscle function (McDonald, 1995, *Am. J. Phys. Med. Rehabil.* (5 Suppl):S70-92). The test can be readily administered by the evaluator (e.g., physician or physical therapist).

5.13 Example 13: Timed Function Tests

Timed function tests include time taken to stand from a supine position, time taken to walk 10 meters, and time taken to climb 4 standard-sized stairs (Mendell, 1989, *N. Engl. J. Med.* 320(24):1592-7; Griggs, 1991, *Arch. Neurol.* 48(4):383-8). These parameters are monitored prior to treatment, on the second to last day of treatment, and during a follow-up period after treatment. During the pre-treatment and treatment periods, the timed function tests are performed prior to the muscle biopsy.

These tests (time taken to stand from supine position, time taken to walk 10 meters, and time taken to climb 4 standard-sized steps) provide an additional measure of functional capability in ambulatory subjects. The tests are reproducible, commonly employed, simple to administer, and have documented response to therapeutic intervention with steroids (Mendell, 1989, *N. Engl. J. Med.* 320(24):1592-7; Griggs, 1991, *Arch. Neurol.* 48(4):383-8).

5.14 Example 14: Serum CK Levels

Serum CK activity is assessed using a commercially available NADH-linked kinetic assay (Diagnostic Chemicals Ltd., Oxford, Conn.). Serum CK levels are measured prior to treatment, on day 1 (prior to first dose), day 7, day 14, day 21, and day 27 during the treatment period, and on day 42 and day 56 after treatment. Serum CK is increased in Duchenne muscular dystrophy and therefore is a readily measurable diagnostic marker for the disease and may serve as a potential biomarker for the pharmacological activity of the drug (Mendell et al., 1989, *New Eng. J. Med.* 320(24): 1592-1597).

Serum CK provides a measure of whole-body muscle integrity. Concentrations of this enzyme in the serum are increased 50- to 100-fold in subjects with DMD and measurements of its levels are used in making an early diagnosis of the disease (Worton, The muscular dystrophies, In: Scriver C. R., Beaudet A. L., Sly W. S., Valle D, eds. The metabolic and molecular basis of inherited disease. 8th ed. Vol. 4. New York: McGraw-Hill, 2001:5493-523). The levels of serum CK are measured to monitor the progression of the disease and serve as a marker for muscle damage. While exercise-induced changes introduce variability (Politano, 2003, *Acta. Myol.* 22(1): 15-21), the marker has advantages because it can be easily, repeatedly, and frequently assessed with a widely available and reliable assay. Prior clinical studies have shown decreases in serum CK coincident with improvements in muscle strength during treatment with steroids (Reitter, 1995, *Brain Dev.* 17 Suppl:39-43).

5.15 Example 15: Dermal Fibroblast and Muscle Cell Culture

Studies are performed on muscle tissue and skin from patients to determine whether dystrophin production in primary muscle cultures from the patients corresponds with dystrophin production in vivo. These experiments evaluate whether dermal fibroblasts from patients, when differentiated into muscle cells in vitro by transfection with a MyoD-producing expression construct (Wang, 2001, *Development* 128: 4623-33), demonstrate dystrophin production in response to treatment. Correlations of skin cell response with clinical activity may offer an easy-to-obtain predictive test in selecting future patients for therapy or for screening new agents for the treatment of DMD. Cells are cultured as follows. Biopsy material is stored during transport in human proliferation medium (or PBS), and on ice for longer time periods if necessary. If the tissue is not prepared within 24 hours, the material can be frozen in human proliferation medium containing 10% DMSO and stored in liquid nitrogen (or dry ice). At the time the tissue is to be prepared for setting up the myoblast culture, biopsy material is washed in PBS. PBS sufficient to keep the tissue moist is added into a culture dish. The biopsy material is minced thoroughly with razor blades, toward an almost homogeneous suspension. Approximately 2 ml of collegenase/dispase/$CaCl_2$ solution per gram of tissue is added and mincing is continued for several minutes (e.g. for a muscle biopsy of 5×5×5 mm use 1 ml of enzyme solution). The suspension is transferred into a sterile tube and incubated at 37° C. in a waterbath until the mixture is a fine slurry (e.g., about 20 to 30 minutes). The suspension is further homogenized by pipetting up and down several times during incubation. Additional resuspension cycles by pipetting up an down with a syringe can be performed if necessary. Eight mL of human proliferation medium is added to the suspension and mixed. The mixture is centrifuged for 10 minutes at 1200 rpm. The cell pellet is resuspended in 3 ml human proliferation medium. Cells are plated into one well of a collagen-coated 6-wells plate, or, depending on the amount of material, in a T25 collagen-coated flask. Cells are cultured for 48 hrs, at 37° C. and 5% $CO_2$. Non-attached cells are removed and transferred to another collagen-coated well (as backup). Fresh proliferation medium is added to the first well (3 ml). The cells are cultured from the first well to confluency and until two confluent T75-flasks have been obtained. For storage, cells can be frozen from one T75 flask into 4 cryotubes with 1 ml freezing medium. The myogenic cell content of the culture is determined by performing a desmin-staining. Preplating of the cultures is required if the percentage of desmin-positive cells is too low.

5.16 Example 16: Phase 2 Study of 3-[5-(2-fluorophenyl)-[1,2,4]oxadiazol-3-yl]-benzoic as an Oral Treatment for Duchenne Muscular Dystrophy Subjects must have met all of the following conditions to be eligible for enrollment into the study:

1. Diagnosis of Duchenne muscular dystrophy (DMD) based on a clinical phenotype presenting by age 5, with increased serum CK and absence of dystrophin on a muscle biopsy (negative sarcolemmal staining with an antibody to the C-terminal portion of the dystrophin protein);
2. Presence of a nonsense mutation in the dystrophin gene;
3. Documentation that dystrophin gene sequencing has been performed or, if sequencing has not already been performed, that a blood sample has been sent for the confirmatory dystrophin gene sequencing;
4. Physical examination or radiographic imaging evidence of EDB muscles in both feet;
5. Ability to ambulate;
6. Male sex;
7. Age ≥5 years;
8. Willingness to abstain from sexual intercourse or employ a barrier or medical method of contraception during the study drug administration and follow-up periods in subjects known to be sexually active;
9. Willingness and ability to comply with scheduled visits, drug administration plan, laboratory tests, study restrictions, and study procedures (including muscle biopsies, myometry, and PK sampling);
10. Able to provide written informed consent if ≥18 years of age, or written informed assent (with parental/guardian consent) if ≥7 years of age. If the subject is ≤7 years of age, parent/legal guardian consent alone will be obtained; and
11. Evidence of personally signed and dated informed consent document (assent also required for children ≥7 years of age) indicating that the subject/parent/legal guardian has been informed of all pertinent aspects of the trial should be followed.

The presence of any of the following conditions will exclude a subject from study enrollment:

1. Prior or ongoing medical condition (e.g., concomitant illness, psychiatric condition, alcoholism, drug abuse), medical history, physical findings, ECG findings, or laboratory abnormality that, in the investigator's opinion, could adversely affect the safety of the subject, makes it unlikely that the course of treatment or follow-up would be completed, or could impair the assessment of study results;
2. Clinical symptoms and signs of congestive cardiac failure (American College of Cardiology/American Heart Association Stage C or Stage D) (Hunt, 2001, *J. Am. Coll. Cardiol.* 38:2101-13);
3. Positive hepatitis B surface antigen, hepatitis C antibody test, or human immunodeficiency virus (HIV) test;
4. Hemoglobin <10 g/dL;
5. Serum albumin <2.5 g/dL;

6. Abnormal GGT or total bilirubin (> laboratory's upper limit of normal);

7. Abnormal renal function (serum creatinine >1.5 times laboratory's upper limit of normal);

8. History of solid organ or hematological transplantation;

9. Ongoing immunosuppressive therapy (other than corticosteroids);

10. Exposure to another investigational drug within 28 days prior to start of study treatment;

11. Ongoing participation in any other therapeutic clinical trial;

12. Ongoing use of thiazolidinedione peroxisome proliferator-activated receptor gamma (PPAR γ) agonists, e.g., rosiglitazone (AVANDIA® or equivalent) or pioglitazone (ACTOS® or equivalent);

13. Change in systemic corticosteroid therapy (e.g., initiation of treatment; cessation of treatment; change in dose, schedule, or type of steroid) within 3 months prior to start of study treatment; or 14. Treatment with systemic aminoglycoside antibiotics within 3 months prior to start of study treatment.

3-[5-(2-Fluoro-phenyl)-[1,2,4]oxadiazol-3-yl]-benzoic acid was provided in a formulation described herein. Treatment was administered over 28 days for each treatment cohort. An initial cohort of patients (n=6) were treated daily for 28 days with 3-[5-(2-fluoro-phenyl)-[1,2,4]oxadiazol-3-yl]-benzoic acid at 4-, 4-, and 8-mg/kg TID. After review of the clinical safety results, a second cohort of patients (n=20) were treated daily for 28 days with 3-[5-(2-fluoro-phenyl)-[1,2,4]oxadiazol-3-yl]-benzoic acid at 10-, 10-, and 20-mg/kg TID. Thus, each patient received a total of 84 doses of 3-[5-(2-fluoro-phenyl)-[1,2,4]oxadiazol-3-yl]-benzoic acid.

Partial restoration or increase in extensor digitorum brevis muscle membrane dystrophin on staining for the C-terminal domain of the protein was demonstrated in some patients at both dose levels on day 28 relative to baseline. The mean pharmacokinetic parameters obtained from the study are set forth below in Table 7 and are also shown in FIG. 1.

at, or within ±5 minutes of, the scheduled time. The timing of the blood draw is in relation to the study drug dosing time.

Each sample comprises 2 mL of venous blood drawn into a 5-mL VACUTAINER® or equivalent tube with $K_3$-EDTA as the anticoagulant. Immediately after collection, the tube is gently inverted 8 to 10 times to mix the anticoagulant with the blood sample. The tube is stored upright on ice until centrifugation; centrifugation and sample processing are performed within 1 hour of sample collection. The plasma fraction is separated by placing the collection tube into a refrigerated centrifuge (4 to 8° C.) in a horizontal rotor (with a swing-out head) for a minimum of 15 minutes at 1500 to 1800 relative centrifugal force (RCF). The plasma fraction is withdrawn by pipette and divided into 2 polypropylene freezing tubes (with each tube receiving approximately equal aliquots). All sample collection and freezing tubes are clearly labeled in a fashion that identifies the subject, the study period, and the collection date and time. Labels are fixed to freezing tubes in a manner that will prevent the label from becoming detached after freezing. After processing, samples are placed into a freezer at approximately −20° C. (or lower).

To protect against sample loss, the samples are divided into 2 shipments, each containing 1 aliquot of plasma for each time point (1 predose aliquot and 1 postdose aliquot). The first aliquots of the samples are shipped within 28 to 30 days of collection. Samples for multiple subjects can be sent together as part of a single shipment. Prior to shipping, the samples are packed in thermal insulated containers with sufficient dry ice to ensure they remain frozen and are protected from breakage during shipment. Samples are shipped overnight via priority courier.

Samples are stored for analysis of 3-[5-(2-fluoro-phenyl)-[1,2,4]oxadiazol-3-yl]-benzoic acid at the end of the study using a validated high performance liquid chromatography with tandem mass spectrometry (HPLC/MS-MS) method. Thereafter, samples are retained for potential later analyses.

TABLE 7

| Parameter | 4, 4, 8 mg/kg | | | 10, 10, 20 mg/kg | | | 20, 20, 40 mg/kg | | |
|---|---|---|---|---|---|---|---|---|---|
| | N = 6 | | | N = 20 | | | N = 11[b] | | |
| | Predicted[a] | Day 1 | Day 28 | Predicted[a] | Day 1 | Day 28 | Predicted[a] | Day 1 | Day 28 |
| $AUC_{0-24}$ μg · hour/mL | 176 | 87 | 91 | 439 | 291 | 235 | 470 | 866 | 490 |
| $C_{max}$ μg/mL | 18 | 10 | 11 | 47 | 27 | 22 | 44 | 76 | 46 |
| $C_{min}$ μg/mL | 7.9 | 0.5 | 0.6 | 19.8 | 3.8 | 3.4 | ** | 9.6 | 6.7 |

[a]Predicted values based on compartmental model derived from results of prior Phase 1 multiple-dose study
[b]Patient 002-010 excluded from analysis due to insufficient data.
Abbreviations:
AUC = area under the concentration-time curve;
$C_{max}$ = maximum concentration;
$C_{min}$ = minimum concentration Blood for 3-[5-(2-fluoro-phenyl)-[1,2,4]oxadiazol-3-yl]-benzoic acid concentrations is collected immediately predose and at 3 hours after administration of the first daily dose of study drug on the second day of each visit.

The study drug dosing and sample collection times are recorded. If a heparinized venous catheter is used for sample collection in order to avoid repeated needle sticks, at least 2 mL of blood is removed and discarded prior to each sample collection in order to avoid heparin contamination of the sample. All attempts are made to collect the blood samples The primary endpoint in the trial was the proportion of patients having an increase in dystrophin expression in muscle during 28 days of treatment with 3-[5-(2-fluoro-phenyl)-[1,2,4]oxadiazol-3-yl]-benzoic acid. Pre- and posttreatment immunofluorescence data from the EDB muscles were available from all 38 patients. As shown in Table 8, the data indicated that, at both dose levels, patients demonstrated qualitative improvement in the staining for dystrophin. Overall, 4 of the 6 (67%) (90% CI 27-94%) patients treated at the 4-, 4-, 8-mg/kg dose level, 10 of the 20 (50%)

(90% CI 30-70%) patients treated at the 10-, 10-, 20-mg/kg dose level, and 6 of the 12 (50%) (90% CI 50-75%) patients treated at the 20-, 20-, 40-mg/kg dose level demonstrated an increase in the expression of dystrophin post-treatment. Response did not appear to be dependent on pre-treatment dystrophin expression (absent vs minimal), age, steroid use, or location or type of nonsense mutation.

Pre-treatment of primary muscle cells from 24 of the 26 boys in the first 2 cohorts were available for in vitro myotube culture. When cultured in the presence of 3-[5-(2-fluoro-phenyl)-[1,2,4]oxadiazol-3-yl]-benzoic acid, myotube cultures showed evidence of a dose-dependent increase in dystrophin expression in response to 3-[5-(2-fluoro-phenyl)-[1,2,4]oxadiazol-3-yl]-benzoic acid treatment. At a concentration of 10 μg/mL, 24 of 24 (100%) showed production of full-length dystrophin, suggesting the potential for nonsense mutation suppression in all subjects if sufficient concentrations are achieved. The majority of subjects receiving the 4-, 4-, 8-mg/kg; the 10-, 10-, 20-mg/kg; or the 20-, 20-, 40-mg/kg dose level had decreases in CK when comparing end-of-treatment values to pretreatment values. These changes were statistically significant (p=0.03, p=0.002, p=0.001 for low-, middle- and high doses, respectively). The return of mean values toward baseline upon cessation of treatment provided additional support for pharmacological activity.

TABLE 8

| Patient Number | Age (years) | Steroid Use | Mutation | Stop Codon Type | In Vivo Expression Response | In Vitro Expression Response |
|---|---|---|---|---|---|---|
| | | | | | Low Dose[a] N = 6 | |
| 001 | 11 | Yes | W1268X | UGA | No | Yes |
| 002 | 10 | Yes | E2035X | UAG | Yes | Yes |
| 001 | 9 | Yes | S3127X | UGA | Yes | Yes |
| 002 | 9 | Yes | W1075X | UAG | Yes | Yes |
| 001 | 6 | Yes | R3381X | UGA | No | ND[b] |
| 002 | 5 | Yes | R3034X | UGA | Yes | ND[b] |
| | | | | | Middle Dose[c] N = 20 | |
| 003 | 10 | No | E2286X | UAA | Yes | Yes |
| 004 | 6 | No | E2035X | UAG | Yes | Yes |
| 005 | 10 | Yes | E1182X | UAG | No | Yes |
| 006 | 9 | No | R3391X | UGA | No | Yes |
| 007 | 9 | Yes | Q1885X | UGA | No | Yes |
| 008 | 9 | Yes | Q2574X | UAG | No | Yes |
| 009 | 8 | No | E2894X | UGA | Yes | Yes |
| 010 | 8 | Yes | R145X | UGA | Yes | Yes |
| 003 | 9 | Yes | W1879X | UGA | Yes | Yes |
| 004 | 13 | Yes | R1844X | UGA | No | Yes |
| 005 | 11 | Yes | Q555X | UAA | Yes | Yes |
| 006 | 8 | Yes | W2925X | UGA | No | Yes |
| 007 | 8 | Yes | W1956X | UAG | No | Yes |
| 008 | 7 | Yes | Y1882X | UAA | Yes | Yes |
| 003 | 8 | Yes | R539X | UGA | No | Yes |
| 004 | 7 | No | Q194X | UAA | Yes | Yes |
| 005 | 7 | Yes | R145X | UGA | Yes | Yes |
| 006 | 12 | Yes | R1967X | UGA | No | Yes |
| 007 | 7 | No | K871X | UGA | Yes | Yes |
| 008 | 11 | No | Q267X | UAG | No | Yes |
| | | | | | High Dose[d] N = 20 | |
| 011 | 6 | Yes | Q2526X | UGA | Yes | Yes |
| 012 | 8 | Yes | R2905X | UGA | Yes | Yes |
| 013 | 8 | Yes | R3034X | UGA | No | Yes |
| 014 | 10 | No | Q555X | UAA | No | NA[e] |
| 015 | 5 | No | Q555X | UAA | No | NA[e] |
| 016 | 9 | Yes | K2791X | UGA | No | NA[e] |
| 009 | 17 | Yes | R2870X | UGA | Yes | Yes |
| 010 | 14 | No | L654X | UGA | Yes | Yes |
| 011 | 14 | No | R1967X | UGA | Yes | ND |
| 012 | 6 | Yes | S147X | UGA | Yes | Yes |
| 009 | 9 | Yes | R3034X | UGA | No | Yes |
| 010 | 9 | Yes | R195X | UGA | No | Yes |

[a]4 mg/kg in the morning, 4 mg/kg at midday, and 8 mg/kg in the evening
[b]Biopsies lost during transportation
[c]10 mg/kg in the morning, 10 mg/kg at midday, and 20 mg/kg in the evening
[d]20 mg/kg in the morning, 20 mg/kg at midday, and 40 mg/kg in the evening
[e]Biopsies not analyzed yet
[f]Biopsy sample not preserved appropriately, thus cells could not be cultured
Abbreviations:
ND = not done For variations of this protocol, at each dose level, it is recommended that 3-[5-(2-fluoro-phenyl)-[1,2,4]oxadiazol-3-yl]-benzoic acid be taken TID at 6-, 6-, and 12-hour (±~30 minutes) intervals. Ideally each dose is taken within ~30 minutes after a meal (e.g., ~7:00 AM after breakfast, ~1:00 PM after lunch, and ~7:00 PM after dinner). While it is realized that variations in dosing schedule may occur in the outpatient setting, it is recommended that the prescribed regimen (including dosing intervals and the relationship of dosing to meals) be followed closely on the days of PK sample collection. Clinical endpoints are evaluated using the procedures set forth above.

5.17 Example 17: Quantitative Cough Assessment

It is commonly acknowledged that excessive coughing compromises how people feel and function. Among the most frequent reason for which patients seek primary care treatment in the United States is coughing (Hing et al., 2006, *Adv. Data* 374:1-33). Patients with chronic cough describe frustration, irritability, anger with the disruptive nature of coughing, and the negative impact on sleep and social interactions (Kuzniar et al., 2007, *Mayo Clin. Proc.* 82(1): 56-60). In patients with cystic fibrosis (CF), cough is among the most prominent of disease-related symptoms, and increases in daytime and nighttime coughing, along with increases in sputum production, are the most common reasons for seeking unscheduled medical care (Sawicki et al., 2006, *Ped. Pulm.*, Suppl. 29:344(#388)). Coughing in CF is likely related to airway obstruction with mucopurulent secretions and to chronic airway inflammation; substantially increased coughing commonly heralds a pulmonary exacerbation and is associated with decreases in $FEV_1$ and increases in inflammatory markers (Smith et al., 2006, *Thorax* 61(5):425-9). Chronic daytime coughing frequencies of 2 to 5 coughs per hour have been documented in CF patients just after they have completed treatment for a pulmonary exacerbation (Id.), but are probably higher in an outpatient setting; normal individuals generally have fewer coughs in an entire day (Hsu et al., 1994, *Eur. Respir. J.* 7(7); 1246-53). Subjective cough assessment is often compromised by patient accommodation to the chronicity of the event and consequent inability to recall how much coughing has occurred; patients tend to underreport coughing episodes and there is often little correlation between objective and subjective cough assessment Id.; Coyle et al., 2005, *Cough* 1:3; Smith et al., 2006, *Thorax* 61(5):425-9).

The VivoMetrics, Inc. LIFESHIRT® is a lightweight, washable vest that is available for patients ≥5 years of age and incorporates motion-sensing transducers, electrodes, a throat microphone, calibration bag, and a 3-axis accelerometer (see LIFESHIRT® Monitoring System QuickStart Guide, incorporated by reference herein in its entirety). Using integrated input from the motion sensors and microphone, the frequency and intensity of cough can be measured. Time-stamped data are stored on a compact flash card housed within the recorder and can be uploaded to the manufacturer, VivoMetrics, Inc., for analysis using specialized software. Data can be transferred to Excel, Oracle or SAS.

The device has proved highly accurate in assessing cough when compared to video/audio evaluations of patients with chronic obstructive pulmonary disease (Coyle et al., 2005, *Cough* 1:3). The device was used to obtain the data set forth in FIG. 2 and will be used to offer substantial supplementary data regarding the clinical benefits of 3-[5-(2-fluoro-phenyl)-[1,2,4]oxadiazol-3-yl]-benzoic acid during Phase 3 testing in CF. Existing informally collected symptom data from the Phase 2 studies of 3-[5-(2-fluoro-phenyl)-[1,2,4]oxadiazol-3-yl]-benzoic acid support this concept. Notably, several patients described on-study decreases in coughing. Without being limited by theory, based on the hypothesis that 3-[5-(2-fluoro-phenyl)-[1,2,4]oxadiazol-3-yl]-benzoic acid-mediated induction of CFTR function would reduce airway obstruction and inflammation, a decrease in cough frequency could serve as a symptomatic integration of these pharmacological effects and might offer a more accurate and quantitative assessment than verbal patient reporting.

It will be appreciated that, although specific embodiments of the invention have been described herein for purposes of illustration, the invention described herein is not to be limited in scope by the specific embodiments herein disclosed. These embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description.

What is claimed is:

1. A method for treating or managing cancer resulting from a nonsense mutation in a patient having cancer resulting from a nonsense mutation, comprising administering to the patient in three doses per day a pharmaceutical composition comprising an effective amount of 3-[5-(2-fluoro-phenyl)-[1,2,4]oxadiazol-3-yl]-benzoic acid or a pharmaceutically acceptable salt thereof, refined polydextrose, mannitol, one or more surfactant agents selected from the group consisting of polyethylene glycol 3350 and poloxamer 407 powder, crospovidone, and one or more other excipients selected from the group consisting of hydroxyethyl cellulose, vanilla flavor, magnesium stearate and colloidal silica, wherein the first dose administered is in a range of about 18 mg/kg to about 22 mg/kg of 3-[5-(2-fluoro-phenyl)-[1,2,4]oxadiazol-3-yl]-benzoic acid or a pharmaceutically acceptable salt thereof, the second dose administered is in a range of about 18 mg/kg to about 22 mg/kg of 3-[5-(2-fluoro-phenyl)-[1,2,4]oxadiazol-3-yl]-benzoic acid or a pharmaceutically acceptable salt thereof and the third dose administered is in a range of about 35 mg/kg to about 40 mg/kg of 3-[5-(2-fluoro-phenyl)-[1,2,4]oxadiazol-3-yl]-benzoic acid or a pharmaceutically acceptable salt thereof, in a plurality of 24 hour time periods, wherein the second dose is administered about 6 hours after the first dose is administered, the third dose is administered about 6 hours after the second dose is administered, and the first dose for a next 24 hour time period is administered about 12 hours after the third dose was administered for a preceding 24 hour time period, and wherein a plasma concentration of 3-[5-(2-fluoro-phenyl)-[1,2,4]oxadiazol-3-yl]-benzoic acid or a pharmaceutically acceptable salt thereof in a range of about 2 µg/mL to about 20 µg/mL is maintained in said patient for a 24 hour time period.

2. The method of claim 1, wherein the cancer is selected from solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia, chronic lymphocytic leukemia, hairy cell leukemia, or multiple myeloma.

3. The method of claim 1, wherein the pharmaceutical composition comprises 3-[5-(2-fluoro-phenyl)-[1,2,4]oxadiazol-3-yl]-benzoic acid 25.0%, refined polydextrose 25.7%, mannitol 25.0%, polyethylene glycol 3350 12.8% and poloxamer 407 powder 3.7%, crospovidone 5.0%, and hydroxyethyl cellulose, vanilla flavor, magnesium stearate and colloidal silica, each less than 2%.

4. The method of claim 1, wherein the pharmaceutical composition comprises from 35 mg to 1400 mg of 3-[5-(2-fluoro-phenyl)-[1,2,4]oxadiazol-3-yl]-benzoic acid or a pharmaceutically acceptable salt thereof.

5. The method of claim 1, wherein the pharmaceutical composition comprises 125 mg, 250 mg or 1000 mg of 3-[5-(2-fluoro-phenyl)-[1,2,4]oxadiazol-3-yl]-benzoic acid or a pharmaceutically acceptable salt thereof.

6. The method of claim 1, wherein the pharmaceutical composition is packaged in a sachet.

7. The method of claim 1, wherein the pharmaceutical composition comprises granules for reconstitution.

8. The method of claim 1, wherein the pharmaceutical composition is reconstituted to achieve at least 30 mL of liquid in the total volume of suspension.

9. The method of claim 1, wherein the pharmaceutical composition is reconstituted using water, milk, a carbonated beverage, juice, apple sauce, baby food or baby formula.

10. The method of claim 1, wherein the first dose of 3-[5-(2-fluoro-phenyl)-[1,2,4]oxadiazol-3-yl]-benzoic acid or a pharmaceutically acceptable salt thereof administered is 20 mg/kg, the second dose is 20 mg/kg and the third dose is 40 mg/kg.

* * * * *